(12) United States Patent
Baiocchi

(10) Patent No.: US 11,925,663 B2
(45) Date of Patent: Mar. 12, 2024

(54) METHODS OF MANAGING TUMOR FLARE IN ADOPTIVE IMMUNOTHERAPY

(71) Applicant: Atara Biotherapeutics, Inc., Thousand Oaks, CA (US)

(72) Inventor: Robert Baiocchi, Dublin, OH (US)

(73) Assignee: Atara Biotherapeutics, Inc., Thousand Oaks, CA (US)

( * ) Notice: Subject to any disclaimer, the term of this patent is extended or adjusted under 35 U.S.C. 154(b) by 439 days.

(21) Appl. No.: 16/755,745

(22) PCT Filed: Oct. 22, 2018

(86) PCT No.: PCT/US2018/056824
§ 371 (c)(1),
(2) Date: Apr. 13, 2020

(87) PCT Pub. No.: WO2019/083866
PCT Pub. Date: May 2, 2019

(65) Prior Publication Data
US 2021/0393683 A1 Dec. 23, 2021

Related U.S. Application Data

(60) Provisional application No. 62/575,803, filed on Oct. 23, 2017.

(51) Int. Cl.
*A61K 35/17* (2015.01)
*A61P 35/00* (2006.01)

(52) U.S. Cl.
CPC .............. *A61K 35/17* (2013.01); *A61P 35/00* (2018.01)

(58) Field of Classification Search
CPC ................................. A61P 35/00; A61K 35/17
See application file for complete search history.

(56) References Cited

U.S. PATENT DOCUMENTS

| | | | |
|---|---|---|---|
| 6,723,695 | B1 | 4/2004 | Burrows et al. |
| 8,425,898 | B2 | 4/2013 | Sampson et al. |
| 9,011,835 | B2 | 4/2015 | Sampson et al. |
| 2004/0265325 | A1 | 12/2004 | Diamond et al. |
| 2014/0086888 | A1 | 3/2014 | Heslop et al. |

FOREIGN PATENT DOCUMENTS

| | | |
|---|---|---|
| JP | 2017-521396 | 8/2017 |
| WO | WO 2012/162620 A1 | 11/2012 |
| WO | WO 2016/007854 | 1/2016 |
| WO | WO 2016/183153 | 11/2016 |

OTHER PUBLICATIONS

The National Cancer Institute Common Toxicity Criteria for Adverse Events v 3.0 ("CTCAEv3") [Retrieved on Jan. 12, 2022] Retrieved from: https://ctep.cancer.gov/protocoldevelopment/electronic_applications/docs/ctcaev3.pdf (Year: 2006).*
Ramsay et al., "Immune dysfunction in chronic lymphocytic leukemia T cells and lenalidomide as an immunomodulatory drug," Haematologica, 94(9) pp. 1198-1202 (Year: 2009).*
The National Cancer Institute Common Toxicity Criteria for Adverse Events v 4.03 ("CTCAEv4.03") [Retrieved on Jan. 28, 2022] Retrieved from: https://evs.nci.nih.gov/ftp1/CTCAE/CTCAE_4.03/CTCAE_4.03_2010-06-14_QuickReference_8.5x11.pdf (Year: 2009).*
Barker et al., "Successful treatment of EBV-associated post-transplantation lymphoma after cord blood transplantation using third-party EBV-specific cytotoxic T lymphocytes," Blood, 116(23) pp. 5045-5049 (Year: 2010).*
National Cancer Institute Thesaurus, Definition Bolus Dose Procedure pp. 1-2 (last modified Feb. 14, 2011) [Retrieved on Jan. 24, 2022] Retrieved from https://nciterms.nci.nih.gov/ncitbrowser/pages/multiple_search.jsf (Year: 2011).*
Chanan-Khan et al., "Tumor flare reaction associated with lenalidomide treatment in patients with chronic lymphocytic leukemia predicts clinical response," Cancer, 117(10) pp. 2127-2135 (Year: 2011).*
Lee et al., "Clinical values for abnormal 18F-FDG uptake in the head and neck region of patients with head and neck squamous cell carcinoma," European J Radiology 83 pp. 1455-1460 (Year: 2014).*
Castillo et al., "The biology and treatment of plasmablastic lymphoma," Blood, 125(15) pp. 2323-2330 (Year: 2015).*
National Clinical Trial 00002663, "Biological Therapy in Treating Patients at High-Risk or With Lymphoma, Lymphoproliferative Disease, or Malignancies" History of Changes to Study, Dec. 2016 [Retrieved on Jan. 12, 2022] https://clinicaltrials.gov/ct2/history/NCT00002663?V_51=View#StudyPageTop (Year: 2016).*
Cheson et al., "Refinement of the Lugano Classification lymphoma response criteria in the era of immunomodulatory therapy," Blood, 128(21) pp. 2489-2496 (Year: 2016).*
Neelapu et al., "Chimeric antigen receptor T-cell therapy—assessment and management of toxicities," Nat. Rev. Clin. Oncology, vol. 15, pp. 47-62 Sep. 19, 2017.*
Prescribing Information for PROVENGE® (Sipuleucel-T ), p. 1 Highlights ("Warnings and Precautions"), Section 6-6.1 ("Adverse Reactions"), Section 17 ("Patient Counseling Information") (Jul. 2017) (Year: 2017).*
Yoshida et al., "Risk of tumor flare after nivolumab treatment in patients with irradiated field recurrence," Med Oncol 34 pp. 1-4 (Jan. 2017) (Year: 2017).*
Taleb et al., "Tumor flare reaction (TFR) in cancer treatments: a systematic review," Annals of Oncology, Immunotherapy of Cancer, 28(5) p. 414 (1 page total) (Year: 2017).*

(Continued)

*Primary Examiner* — Daniel C Gamett
(74) *Attorney, Agent, or Firm* — Jones Day

(57) ABSTRACT

Provided herein are methods of treating a solid malignant tumor using antigen-specific T cells and methods of managing tumor flare in treatment of a solid malignant tumor using antigen-specific T cells. The methods provided herein improve the safety of treatment by informing the patient about the potential risks for tumor flare, telling the patient to contact his or her physician if tumor swelling occurs, counseling a patient with Waldeyer's ring lymphadenopathy to contact his or her physician if shortness of breath or stridor occurs, or grading and managing tumor flare developed in the patient.

25 Claims, 1 Drawing Sheet

(56) References Cited

OTHER PUBLICATIONS

Stanton et al., J Immunother Cancer. May 17, 2016;4:27 (Year: 2016).*
"Biological therapy in treating patients at high-risk or with lymphoma, lymphoproliferative disease, or malignancies," ClinicalTrials.gov, accessed at https://clinicaltrials.gov/ct2/show/NCT00002663?term=NCT00002663&rank=1, accessed on Oct. 21, 2014, 5 pages.
"Busulfan, melphalan, fludarabine and T-cell depleted allogeneic hematopoietic stem cell transplantation followed by post transplantation donor lymphocyte infusions," ClinicalTrials.gov, accessed at https://www.clinicaltrials.gov/ct2/show/NCT01131169?term=NCT01131169&rank=1, accessed on Jan. 5, 2015, 5 pages.
"Dose escalation trial of WT1-sensitized T cells for residual or relapsed leukemia after allogeneic hematopoietic progenitor cell transplantation," ClinicalTrials.gov, accessed at https://clinicaltrials.gov/ct2/show/NCT00620633?term=NCT00620633&rank=1, accessed on Oct. 3, 2016, 4 pages.
"Dose escalation trial of WT1-specific donor-derived T cells following-cell depleted allogeneic hematopoietic stem cell transplantation for patients with relapsed/refractory multiple myeloma," ClinicalTrials.gov, accessed at https://clinicaltrials.gov/ct2/show/NCT01758328?term=NCT01758328&rank=1, accessed on Oct. 3, 2016, 4 pages.
"Form S-1 Registration Statement," filed with the United States Securities and Exchange Commission by Atara Biotherapeutics, Inc., dated Jun. 29, 2015, 203 pages.
"Primary transplant donor derived CMVpp65 specific T-cells for the treatment of CMV infection or persistent CMV viremia after allogeneic hematopoietic stem cell transplantation," ClinicalTrials.gov, accessed at http://www.clinicaltrials.gov/ct2/show/NCT01646645?term=NCT01646645&rank=1, accessed on Oct. 21, 2014, 4 pages.
"Therapeutic effects of Epstein-Barr virus immune T-lymphocytes derived from a normal HLA-compatible or partially-matched third-party donor in the treatment of EBV lymphoproliferative disorders and EBV-associated malignancies," ClinicalTrials.gov, accessed at http://www.clinicaltrials.gov/ct2/show/NCT01498484?term=NCT01498484&rank=1, accessed on Oct. 21, 2014, 5 pages.
"Trial of third party donor derived CMVpp65 specific T-cells for the treatment of CMV infection or persistent CMV viremia after allogeneic hematopoietic stem cell transplantation," ClinicalTrials.gov, accessed at https://clinicaltrials.gov/ct2/show/NCT02136797?term=NCT02136797&rank=1, accessed on Nov. 10, 2014, 4 pages.
Amarnath and Fowler, Jan. 2012, "Harnessing autophagy for adoptive T cell therapy," Immunotherapy, 4(1):1-4.
American Association for Cancer Research (AACR) Press Release entitled "New T cell-based immunotherapy shows promise for lethal stem cell transplant complication," dated Apr. 19, 2015, 3 pages.
Balduzzi et al., Jul. 2011, "Polyomavirus JC-targeted T-cell therapy for progressive multiple leukoencephalopathy in a hematopoietic cell transplantation recipient," Bone Marrow Transplantation, 46(7):987-992.
Bao et al., Apr. 2012, "Adoptive immunotherapy with CMV specific cytotoxic T lymphocytes for stem cell transplant patients with refractory CMV infections," Journal of Immunotherapy, 35(3):293-298.
Barker et al., Dec. 2010, "Successful treatment of EBV-associated posttransplantation lymphoma after cord blood transplantation using third-party EBV-specific cytotoxic T lymphocytes," Blood, 116(23):5045-5049 (Published online Sep. 8, 2010).
Blyth et al., Nov. 2011, "BK virus-specific T cells for use in cellular therapy show specificity to multiple antigens and polyfunctional cytokine responses," Transplantation, 92(10): 1077-1084.
Burns and Crawford, Sep. 2004, "Epstein-Barr virus-specific cytotoxic T-lymphocytes for adoptive immunotherapy of post-transplant lymphoproliferative disease," Blood Reviews, 18(3):193-209.
Cobbold et al., Aug. 2005, "Adoptive transfer of cytomegalovirus-specific CTL to stem cell transplant patients after selection by HLA-peptide tetramers," The Journal of Experimental Medicine, 202(3):379-386.

Comoli et al., Apr. 2002, "Infusion of autologous Epstein-Barr virus (EBV)-specific cytotoxic T cells for prevention of EBV-related lymphoproliferative disorder in solid organ transplant recipients with evidence of active virus replication," Blood, 99(7):2592-2598.
Cortivo et al., Nov. 2012, "Anti CMV and/or anti adenovirus IFN-g-positive CD4+ CD8+ T lymphocytes for treatment of viral infections after allogeneic HSC transplantation: first results," Blood, 120(21):1906.
Doubrovina et al., Nov. 2004, "In vitro stimulation with WT1 peptide-loaded Epstein-Barr virus-positive B cells elicits high frequencies of WT1 peptide-specific T cells with in vitro and in vivo tumoricidal activity," Clinical Cancer Research, 10(21):7207-7219.
Doubrovina et al., Nov. 2007, "Leukemia-reactive cytotoxic CD8+ and CD4+ T-cells specific for novel WT-1 epitopes are generated in vitro by sensitization with overlapping pentadecapeptides (15-mers) spanning the wilms tumor protein," Blood, 110 (11):1810.
Doubrovina et al., Aug. 2012, "Mapping of novel peptides of WT-1 and presenting HLA alleles that induce epitope-specific HLA-restricted T cells with cytotoxic activity against WT-1(+) leukemias," Blood, 120(8):1633-1646 (Published online May 23, 2012).
Doubrovina et al., Mar. 2012, "Adoptive immunotherapy with unselected or EBV-specific T cells for biopsy-proven EBV+ lymphomas after allogeneic hematopoietic cell transplantation," Blood, 119(11):2644-2656 (Published online Dec. 2, 2011).
Einsele et al., Jun. 2002, "Infusion of cytomegalovirus (CMV)-specific T cells for the treatment of CMV infection not responding to antiviral chemotherapy," Blood, 99(11):3916-3922.
Eiz-Vesper et al., Jan. 2013, "Adoptive T-cell immunotherapy from third-party donors: characterization of donors and set up of a T-cell donor registry," Frontiers in Immunology, 3:410.
Feuchtinger et al., Nov. 2010, "Adoptive transfer of pp65-specific T cells for the treatment of chemorefractory cytomegalovirus disease or reactivation after haploidentical and matched unrelated stem cell transplantation," Blood, 116(20):4360-4367 (Published online Jul. 12, 2010).
Gahn et al., Jan. 2002, "Immunotherapy to reconstitute immunity to DNA viruses," Seminars in Hematology, 39(1):41-47.
Gandhi et al., May 2007, "Immunity, homing and efficacy of allogeneic adoptive immunotherapy for posttransplant lymphoproliferative disorders," American Journal of Transplantation, 7(5):1293-1299 (Published online Apr. 8, 2007).
Gerdemann et al., Jan. 2013, "Immunotherapeutic strategies to prevent and treat human herpesvirus 6 reactivation after allogeneic stem cell transplantation," Blood, 121(1):207-218.
Gottschalk et al., Jan. 2015, "Adoptive T-cell immunotherapy," Current Topics in Microbiology and Immunology, 391:427-454.
Gupta et al., "Treatment of cytomegalovirus (CMV) retinitis with third party donor-derived CMV-specific cytotoxic T-lymphocytes," meeting abstract for ASRS 33rd Annual Meeting held Jul. 11-14, 2015, Vienna, Austria, released on Jul. 1, 2015, 2 pages.
Gupta et al., Jan. 2015, "Treatment of cytomegalovirus retinitis with cytomegalovirus-specific T-lymphocyte infusion," Ophthalmic Surgery, Lasers & Imaging Retina, 46(1):80-82.
Haque et al., Oct. 2001, "Complete regression of posttransplant lymphoproliferative disease using partially HLA-matched Epstein Barr virus-specific cytotoxic T cells," Transplantation, 72(8):1399-1402.
Haque et al., Aug. 2002, "Treatment of Epstein-Barr-virus-positive post-transplantation lymphoproliferative disease with partly HLA-matched allogeneic cytotoxic T cells," Lancet, 360(9331):436-442.
Haque et al., Aug. 2007, "Allogeneic cytotoxic T-cell therapy for EBV-positive posttransplantation lymphoproliferative disease: results of a phase 2 multicenter clinical trial," Blood, 110(4):1123-1131 (Published online Apr. 27, 2007).
Hasan et al., Aug. 2009, "A panel of artificial APCs expressing prevalent HLA alleles permits generation of cytotoxic T cells specific for both dominant and subdominant viral epitopes for adoptive therapy," The Journal of Immunology, 183(4):2837-2850 (Published online Jul. 27, 2009).
Hasan et al., Nov. 15, 2013, "Generation and characterization of a third party GMP grade bank of CMV specific T-cells for adoptive immunotherapy of CMV infections in recipients of HSCT from cord blood or seronegative donors," Blood, 122(21):2021.

(56) References Cited

OTHER PUBLICATIONS

Hasan et al., Dec. 2014, "Banked, GMP grade third party T-cell lines specific for CMVpp65 epitopes presented by certain prevalent HLA alleles more consistently clear CMV infections in a genetically heterogeneous population of HSCT recipients," Blood, 124(21):309.
Hasan et al., Feb. 2014, "Generation and characterization of a third party GMP grade bank of CMV specific T-cells for adoptive immunotherapy of CMV infections in recipients of HSCT from cord blood or seronegative donors," Biology of Blood and Marrow Transplantation, 20(2):S131-S132.
Hasan et al., 2014, "Banked, GMP grade third party T-cell lines specific for CMVpp65 epitopes presented by certain prevalent HLA alleles more consistently clear CMV infections in a genetically heterogeneous population of HSCT recipients," meeting abstract for the 56th American Society of Hematology (ASH) Annual Meeting and Exposition held in San Francisco, California, Dec. 6-9, 2014, first published online on Nov. 6, 2014, 2 pages.
Hasan, "Banked, GMP grade third party T-cell lines specific for CMVpp65 epitopes presented by certain prevalent HLA alleles more consistently clear CMV infections in a genetically heterogeneous population of HSCT recipients," slide presentation on Dec. 8, 2014 at the 56th ASH Annual Meeting held Dec. 6-9, 2014, San Francisco, California, United States, 22 pages.
Heslop et al., Feb. 2010, "Long-term outcome of EBV-specific T-cell infusions to prevent or treat EBV-related lymphoproliferative disease in transplant recipients," Blood, 115(5):925-935 (Published online Oct. 30, 2009).
Holmes-Liew et al., Mar. 2015, "Adoptive T-cell immunotherapy for ganciclovir-resistant CMV disease after lung transplantation," Clinical & Translational Immunology, 4(3):e35.
Humar et al., Dec. 2009, "Cytomegalovirus in solid organ transplant recipients," American Journal of Transplantation, 9(Suppl 4):S78-S86.
International Preliminary Report on Patentability dated Apr. 28, 2020 of International application No. PCT/US2018056824, 6 pages.
International Search Report dated Jan. 30, 2019 of International application No. PCT/US2018056824, 4 pages.
Kawakami et al., Oct. 2005, "A case of immune recovery vitritis induced by donor leukocyte infusion for the treatment of cytomegalovirus retinitis," European Journal of Haematology, 75(4):352-354.
Khanna et al., Aug. 1999, "Activation and adoptive transfer of Epstein-Barr virus-specific cytotoxic T cells in solid organ transplant patients with posttransplant lymphoproliferative disease," Proceedings of the National Academy of Sciences of the United States of America, 96(18):10391-10396.
Kiss et al., "Treatment of cytomegalovirus (CMV) retinitis with systemic infusion of third party donor-derived CMV-specific cytotoxic T-lymphocytes," meeting abstract for The Retina Society 48th Annual Scientific Meeting held Oct. 7-11, 2015, Paris, France, released Oct. 7, 2015, 1 page.
Koehne et al., Jul. 2000, "Rapid selection of antigen-specific T lymphocytes by retroviral transduction," Blood, 96(1):109-117.
Koehne et al., Mar. 2002, "Quantitation, selection, and functional characterization of Epstein-Barr virus-specific and alloreactive T cells detected by intracellular interferon-gamma production and growth of cytotoxic precursors," Blood, 99(5):1730-1740.
Koehne et al., Sep. 2015, "Immunotherapy with donor T cells sensitized with overlapping pentadecapeptides for treatment of persistent cytomegalovirus infection or viremia," Biology of Blood and Marrow Transplantation, 21(9):1663-1678 (Published online May 29, 2015).
Leen et al, Jun. 2013, "Multicenter study of banked third-party virus-specific T cells to treat severe viral infections after hematopoietic stem cell transplantation," Blood, 121(26):5113-5123 (Published online Apr. 22, 2013).
Leen et al., Oct. 2006, "Monoculture-derived T lymphocytes specific for multiple viruses expand and produce clinically relevant effects in immunocompromised individuals," Nature Medicine, 12(10):1160-1166 (Published online Sep. 24, 2006).

Louis et al., Nov.-Dec. 2010, "Adoptive transfer of EBV-specific T cells results in sustained clinical responses in patients with locoregional nasopharyngeal carcinoma," Journal of Immunotherapy, 33(9):983-990.
Lucas et al., Mar. 1996, "The development of cellular immunity to Epstein-Barr virus after allogeneic bone marrow transplantation," Blood, 87(6):2594-2603.
Macesic et al., Mar. 2015, "Adoptive T cell immunotherapy for treatment of ganciclovir-resistant cytomegalovirus disease in a renal transplant recipient," American Journal of Transplantation, 15(3):827-832 (Published online Feb. 3, 2015).
Micklethwaite et al., Jun. 2007, "Ex vivo expansion and prophylactic infusion of CMV-pp65 peptide-specific cytotoxic T-lymphocytes following allogeneic hematopoietic stem cell transplantation," Biology of Blood and Marrow Transplantation, 13(6):707-714 (Published Apr. 6, 2007).
O'Reilly et al., 2016, "Virus-specific T-cell banks for 'off the shelf' adoptive therapy of refractory infections", Bone Marrow Transplantation, 51(9):1163-1172.
O'Reilly et al., May 2007, "Adoptive transfer of antigen-specific T-cells of donor type for immunotherapy of viral infections following allogeneic hematopoietic cell transplants," Immunologic Research, 38(1-3):237-250.
O'Reilly et al., Jun. 2010, "Adoptive transfer of unselected or leukemia-reactive T-cells in the treatment of relapse following allogeneic hematopoietic cell transplantation," Seminars in Immunology, 22(3):162-172 (Published online May 26, 2010).
O'Reilly et al., Sep. 2011, "Novel strategies for adoptive therapy following HLA disparate transplants," Best Practice & Research Clinical Haematology, 24(3):381-391.
O'Reilly et al., Jun. 2015, "T-cell depleted allogeneic hematopoietic cell transplants as a platform for adoptive therapy with leukemia selective or virus-specific T-cells," Bone Marrow Transplant, 50(Suppl 2):S43-S50.
O'Reilly, meeting abstract for the oral presentation on Oct. 31, 2014 at The 76th Annual Meeting of the Japanese Society of Hematology, held Oct. 31-Nov. 2, 2014, Osaka, Japan, 1 page.
Papadopoulou et al., Jun. 2014, "Activity of broad-spectrum T cells as treatment for AdV, EBV, CMV, BKV, and HHV6 infections after HSCT," Science Translational Medicine, 6(242):242ra83.
Peggs et al., Oct. 2003, "Adoptive cellular therapy for early cytomegalovirus infection after allogeneic stem-cell transplantation with virus-specific T-cell lines," Lancet, 362(9393):1375-1377.
Prockop et al., "Banked EBV-specific T-cells from HLA-partially matched normal donors induce durable remissions of rituximab refractory EBV+ B-cell lymphomas post hematopoietic and organ allografts," meeting abstract for the 2015 ASCO Anual Meeting held May 29-Jun. 2, 2015, Chicago, Illinois, United States, published May 20, 2015 (the same abstract was published online early on May 13, 2015), 2 pages.
Prockop et al., "Epstein-Barr virus-specific cytotoxic T lymphocytes for treatment of rituximab-refractory Epstein-Barr virus-associated lymphoproliferative disorder," meeting abstract for the 2015 AACR Anual Meeting held Apr. 18-22, 2015, Philadelphia, Pennsylvania, United States, published Mar. 18, 2015, 2 pages.
Prockop et al., Dec. 2014, "Third party donor derived CMV specific T cells for the treatment of refractory CMV viremia and disease after hematopoietic stem cell transplant," Blood, 124(21):184.
Prockop et al., Feb. 2014, "Third party donor derived EBV specific T cells for the treatment of refractory EBV-related post-transplant lymphomas," Biology of Blood and Marrow Transplantation, 20(2):S49-S50.
Prockop et al., 2014, "Third party donor derived CMV specific T cells for the treatment of refractory CMV viremia and disease after hematopoietic stem cell transplant," meeting abstract for the 56th American Society of Hematology (ASH) Annual Meeting and Exposition held in San Francisco, California, Dec. 6-9, 2014, first published online on Nov. 6, 2014, 2 pages.
Prockop et al., Dec. 2015, "Successful treatment of refractory CMV chorioretinitis and meningoencephalitis with adoptive transfer of third party CMVpp65 specific T-cell lines," Blood, 126(23):3157.
Prockop et al., 2015, "Successful treatment of refractory CMV chorioretinitis and meningoencephalitis with adoptive transfer of

(56) References Cited

OTHER PUBLICATIONS third party CMVpp65 specific T-cell lines," meeting abstract for the 57th American Society of Hematology (ASH) Annual Meeting and Exposition held in Orlando, Florida, Dec. 5-8, 2015, first published online on Nov. 5, 2015, 3 pages.

Prockop, "3rd party CMV specific T cells for the treatment of refractory CMV viremia and disease after HSCT," slide presentation on Dec. 7, 2014 at the 56th ASH Annual Meeting held Dec. 6-9, 2014, San Francisco, California, United States, 27 pages.

Prockop, "Efficacy and Safety of ATA129, Partially Matched Allogeneic Third-Party Epstein-Barr Virus-Targeted Cytotoxic T Lymphocytes in a Multicenter Study for Post-Transplant Lymphoproliferative Disorder," Abstract 4520 for presentation on Dec. 11, 2017 at the 56th American Society of Hematology Annual Meeting held Dec. 6-12, 2014, San Francisco, California, United States, accessed at https://ash.confex.com/ash/2017/webprogram/Paper107933.html on Nov. 30, 2017, 2 pages.

Prockop, "Adoptive immunotherapy with banked virus specific 3rd party donor T-cells for CMV infections and EBV LPD complicating hematopoietic cell transplants," slide presentation on Oct. 31, 2014 at The 76th Annual Meeting of the Japanese Society of Hematology, held Oct. 31-Nov. 2, 2014, Osaka, Japan, 43 pages.

Prockop, "Banked EBV-specific T-cells from HLA-partially matched normal donors induce durable remissions of rituximab refractory EBV+ B-cell lymphomas post hematopoietic and organ allografts," slide presentation on Jun. 1, 2015 at the 2015 ASCO Annual Meeting held May 29-Jun. 2, 2015, Chicago, Illinois, United States, 18 pages.

Prockop, "Epstein-Barr virus (EBV)-specific cytotoxic T lymphocytes (EBV-CTLs) for treatment of rituximab-refractory EBV-associated lymphoproliferative disorder (EBV-LPD)," slide presentation on Apr. 19, 2015 at the 2015 AACR Annual Meeting held Apr. 18-22, 2015, Philadelphia, Pennsylvania, United States, 25 pages.

Prockop, "Third party donor derived EBV specific T cells for the treatment of refractory lymphoma in immunodeficient recipients," slide presentation on Mar. 1, 2014 at the ASBMT 2014 BMT Tandem Meetings held Feb. 26-Mar. 2, 2014, Grapevine, Texas, United States, 22 pages.

Prockop, "Third party donor T cells for the treatment of CMV infection and EBV lymphoma in immunodeficient patients," slide presentation on May 22, 2014 at the 9th Meeting of the EBMT Pediatric Diseases WP, held May 21-23, 2014, Jerusalem, Israel, 47 pages.

Prockop, 2016, "Treatment of EBV+ nasopharyngeal carcinoma with banked EBV-specific cytotoxic T cells", J Clin Oncol, 34(15 Suppl): Abstract 3012.

Qasim et al., May 2013, "Interferon-γ capture T cell therapy for persistent Adenoviraemia following allogeneic haematopoietic stem cell transplantation," British Journal of Haematology, 161(3):449-452 (Published online Feb. 22, 2013).

Ramos et al., Jan. 2013, "Human papillomavirus type 16 E6/E7-specific cytotoxic T lymphocytes for adoptive immunotherapy of HPV-associated malignancies," Journal of Immunotherapy, 36(1):66-76.

Rooney et al., Jan. 1995, "Use of gene-modified virus-specific T lymphocytes to control Epstein-Barr-virus-related lymphoproliferation," Lancet, 345(8941):9-13.

Rooney et al., Sep. 1998, "Infusion of cytotoxic T cells for the prevention and treatment of Epstein-Barr virus-induced lymphoma in allogeneic transplant recipients," Blood, 92(5):1549-1555.

Schmitt et al., Mar. 2011, "Adoptive transfer and selective reconstitution of streptamer-selected cytomegalovirus-specific CD8+ T cells leads to virus clearance in patients after allogeneic peripheral blood stem cell transplantation," Transfusion, 51(3):591-599 (Published online Dec. 6, 2010).

Sili et al., Jan. 2012, "Production of good manufacturing practice-grade cytotoxic T lymphocytes specific for Epstein-Barr virus, cytomegalovirus and adenovirus to prevent or treat viral infections post-allogeneic hematopoietic stem cell transplant," Cytotherapy, 14(1):7-11.

Straathof et al., Mar. 2005, "Treatment of nasopharyngeal carcinoma with Epstein-Barr virus--specific T lymphocytes," Blood, 105(5):1898-1904 (Published online Nov. 12, 2004).

Sukdolak et al., Oct. 2013, "CMV-, EBV- and ADV-specific T cell immunity: screening and monitoring of potential third-party donors to improve post-transplantation outcome," Biology of Blood and Marrow Transplantation, 19(10):1480-1492 (Published online Jul. 23, 2013).

Trivedi et al., Apr. 2005, "Generation of CMV-specific T lymphocytes using protein-spanning pools of pp65-derived overlapping pentadecapeptides for adoptive immunotherapy," Blood, 105(7):2793-2801 (Published online Oct. 28, 2004).

Tse and Kwong, Jan. 2015, "Epstein Barr virus-associated lymphoproliferative diseases: the virus as a therapeutic target," Experimental & Molecular Medicine, 47:e136.

Uhlin et al., Oct. 2012, "Rapid salvage treatment with virus-specific T cells for therapy-resistant disease," Clinical Infectious Diseases, 55(8):1064-1073 (Published online Jul. 17, 2012).

Waldrop et al., Apr. 1997, "Determination of antigen-specific memory/ effector CD4+ T cell frequencies by flow cytometry: evidence for a novel, antigen-specific homeostatic mechanism in HIV-associated immunodeficiency," Journal of Clinical Investigation, 99(7):1739-1750.

Walter et al., Oct. 1995, "Reconstitution of cellular immunity against cytomegalovirus in recipients of allogeneic bone marrow by transfer of T-cell clones from the donor," The New England Journal of Medicine, 333(16):1038-1044.

Wilkie et al., Jul.-Aug. 2004, "Establishment and characterization of a bank of cytotoxic T lymphocytes for immunotherapy of epstein-barr virus-associated diseases," Journal of Immunotherapy, 27(4):309-316.

Written Opinion dated Jan. 30, 2019 of International application No. PCT/US2018056824, 5 pages.

Yoshida et al., 2017, "Risk of tumor flare after nivolumab treatment in patients with irradiated field recurrence", Med Oncol, 34:34 (4 pages).

"Questions and Answers—Provenge," accessed on Apr. 7, 2022 at: https://www.fda.gov/vaccines-blood-biologics/cellular-gene-therapy-products/questions-and-answers-provenge (content current as of Mar. 16, 2018), 3 pages.

Anassi and Ndefo, 2011, "Sipuleucel-T (Provenge) injection: the first immunotherapy agent (vaccine) for hormone-refractory prostate cancer," Pharmacy and Therapeutics 36(4):197-202.

Ferrajoli et al., 2008, "Lenalidomide induces complete and partial remissions in patients with relapsed and refractory chronic lymphocytic leukemia," Blood 111(11): 5291-5297.

Kawada et al., 2016, "Mechanisms underlying 18F-fluorodeoxyglucose accumulation in colorectal cancer," World J Radiol 8(11): 880-886.

Ansell et al., "PD-1 Blockade with Nivolumab in Relapsed or Refractory Hodgkin's Lymphoma," *The New England Journal of Medicine*, 372:4 (2015) 311-319.

Chong et al., "Chimeric Antigen Receptor Modified T Cells Directed Against CD19 (CTL019) in Patients with Poor Prognosis, Relapsed or Refractory CD19+ Follicular Lymphomas: Prolonged Remissions Related to Antecedent Therapy," *Blood*, 128:22 (2016) 1100.

Curran et al., "Mechanisms or Immune Tolerance in Leukemia and Lymphoma," *Trends in Immunology*, 38:7 (Jul. 2017) 513-525.

Ferlazzo et al., "Cross-talks Between Natural Killer Cells and Distinct Subsets of Dendritic Cells," *Frontiers in Immunology,* vol. 5 (Apr. 2014) Article 159, 1-7.

Hofman et al., "How We Read Oncologic FDG PET/CT," *Cancer Imaging,* 16:35 (2016) 1-14.

Hsu et al., "The Immunostimulatory Effect of Lenalidomide on NK-Cell Function is Profoundly Inhibited by Concurrent Dexamethasone Therapy," *Blood,* 117:5 (Feb. 3, 2011) 1605-1613.

Kalos et al., "T Cells with Chimeric Antigen Receptors have Potent Antitumor Effects and can Etablish Memory in Patients with Advanced Leukemia," *Science Translational Medicine* 3:95ra73 (Aug. 10, 2011) 1-21.

Katz et al., "Brentuximab Vedotin (SGN-35)," *Clinical Cancer Research,* 17:20 (Oct. 15, 2011) 6428-6436.

Kochenderfer et al., "Chemotherapy-Refractory Diffuse Large B-Cell Lymphoma and Indolent B-Cell Malignancies can be Effectively

(56) References Cited

OTHER PUBLICATIONS

Treated with autologous T Cells Expressing an Anti-CD19 Chimeric Antigen Receptor," *Journal of Clinical Oncology*, 33:6 (Feb. 20, 2015) 540-549.
Lesokhin et al., "Nivolumab in Patients With Relapsed or Refractory Hematologic Malignancy: Preliminary Results of a Phase Ib Study," *Journal of Clinical Oncology*, 34:23 (2016) 2698-2704.
Liu et al., "Increased Expression of Programmed Cell Death Protein 1 on NK Cells Inhibits NK-Cell- Mediated Anti-Tumor Function and Indicates Poor Prognosis in Digestive Cancers," Oncogene, 36 (Nov. 2017, published online Jul. 2017) 6143-6153.
Locke et al., "Phase 1 Results of ZUMA-1: A Multicenter Study of KTE-C19 Anti-CD19 Car T Cell Therapy in Refractory Aggressive Lymphoma," *Molecular Therapy*, 25:1 (Jan. 2017) 285-295.
Makita et al., "Clinical Development of anti-CD19 Chimeric Antigen Receptor T-Cell Therapy for B-Cell Non-Hodgkin Lymphoma," *Cancer Science*, 108:6 (Jun. 2017) 1109-1118.
Moretta et al., "NK Cells at the Interface Between Innate and Adaptive Immunity," *Cell Death and Differentiation*, 15 (2008) 226-233.
Neelapu et al., "Kte-C19 (Anti-CD19 Car T Cells) Induces Complete Remissions in Patients with Refractory Diffuse Large B-Cell Lymphoma (DLBCL): Results from the Pivotal Phase 2 Zuma-1," *Blood*, 128:11 (2016) LBA-6.
Pardoll, "The Blockade of Immune Checkpoints in Cancer Immunotherapy," *Nature Review Cancer*, 12:4 (2012) 252-264.
Porter et al., "Chimeric Antigen Receptor T Cells Persist and Induce Sustained Remissions in Relapsed Refractory Chronic Lympocytic Leukemia," *Science Translational Medicine*, 7:303ra139 (Sep. 2, 2015) 1-25.
Postow et al., "Immune Checkpoint Blockade in Cancer Therapy," *Journal of Clinical Oncology*, 33:17 (Jun. 10, 2015) 1974-1982.
Schuster et al., "Sustained Remissions Following Chimeric Antigen Receptor Modified T Cells Directed Against CD19 (CTL019) in Patients with Relapsed or Refractory DC19+ Lymphomas," *Blood*, 126:23 (2015) 183.
Schuster et al., "Phase IIa Trial of Chimeric Antigen Receptor Modified T Cells Directed Against CD19 (CTL019) in Patients with Relapsed or Refractory DC19+ Lymphomas," *Journal of Clinical Oncology* 33:15 Suppl (May 20, 2015) 8516.
Schuster et al., "Treatment with Chimeric Antigen Receptor Modified T Cells Directed Against CD19 (CTL019) Results in Durable Remissions in Patients with Relapsed or Refractory Diffuse Large B Cell Lymphomas of Germinal Center and Non-Germinal Center Original, 'Double Hit' Diffuse Large B Cell Lymphomas, and Transformed Follicular to Diffuse Large B Cell Lymphomas," *Blood*, 128:22 (2016) 3026.
Turtle et al., "Immunotherapy of non-Hodkin Lymphoma with a Defined Ratio of CD8+ and CD4+ CD19-specific Chimeric Antigen Receptor-Modified T Cells," *Science Translational Medicine*, 8:355ra116 (Sep. 7, 2016).
Turtle et al., "Biomarkers of Cytokine Release Syndrome and Neurotoxicity After CD19 Car-T Cells and Mitigation of Toxicity by Cell Dose," *Blood*, 128:22 (2016) 1852.
Van Meerten et al., "Complement-Induced Cell Death by Rituximab Depends on CD20 Expression Level and Acts Complementary to Antibody-Dependent Cellular Cytotoxicity," *Clinical Cancer Research*, 12:13 (Jul. 1, 2006) 4027-4035.
Weng et al., "Two Immunoglobulin G Fragment C Receptor Polymorphisms Independently Predict Response to Rituximab in Patients with Follicular Lymphoma," *Journal of Clinical Oncology*, 21:21 (Nov. 1, 2003) 3940-3947.
Westin et al., "Safety and Activity of PD1 Blockade by Pidilizumab in Combination with Rituximab in Patients with Relapsed Follicular Lymphoma: a Single Group, Open-label, Phase 2 Trial," *The Lancet Oncology*, 15:1 (2014) 69-77.
Wierda et al., "Chronic Lymphocytic Leukemia/Small Lymphocytic Lymphoma, Version 1.2017: featured Updates to the NCCN Guidelines," *Journal of the National Comprehensive Cancer Network*, 15:3 (Mar. 2017) 293-311.
Zelenetz et al., "Diffuse Large B-Cell Lymphoma Vrsion 1.2016: Clinical Practice Guidelines in Oncology," *Journal of the National Comprehensive Cancer Network*, 14:2 (Feb. 2016) 196-231.

\* cited by examiner

A. Day 1

D1 CTL #1 infusion
10x8x5
No erythema

B. Day 5

D4 CTL #1 infusion
10x8x7
+erythema, +pain
More diffuse neck erythema

C. Day 8

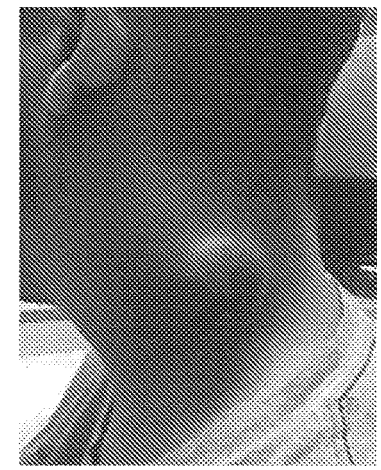

D8 CTL #2 Infusion 10:00
9x8x4
Some erythema, soft
New central necrosis w
Skin breakdown

D. Day 8

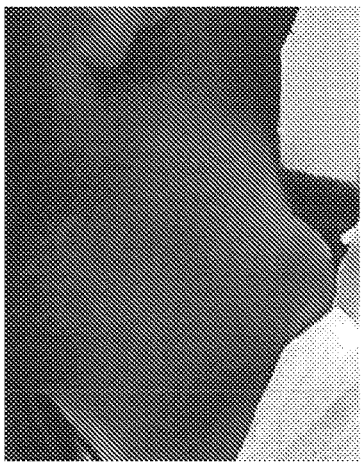

D8 CTL #2 Infusion 13:30
11x10x4
Firm, erythematous, warm
More anterior neck edema
Clear airway, Admit for obs

E. Day 15

D15 CTL #3 infusion
10x10x4: well circumcribed
Ctrl necr, soft, less pain
Serosanguinous drainage

F. Day 18

D18 CTL #3 infusion
10x10x4: well circumcribed
More necrotic ctr
No drainage

METHODS OF MANAGING TUMOR FLARE IN ADOPTIVE IMMUNOTHERAPY

CROSS-REFERENCE TO RELATED APPLICATIONS

This application is a national stage of International Patent Application No. PCT/US2018/056824, filed Oct. 22, 2018, which claims the benefit of U.S. Provisional Application No. 62/575,803, filed Oct. 23, 2017, which is incorporated by reference herein in its entirety.

1. FIELD

Provided herein are methods of treating a solid malignant tumor using antigen-specific T cells and methods of managing tumor flare in treatment of a solid malignant tumor using antigen-specific T cells. The methods provided herein improve the safety of treatment by informing the patient about the potential risks for tumor flare, telling the patient to contact his or her physician if tumor swelling occurs, counseling a patient with Waldeyer's ring lymphadenopathy to contact his or her physician if shortness of breath or stridor occurs, or grading and managing tumor flare developed in the patient.

2. BACKGROUND

Antigen-specific T cells have been used in adoptive immunotherapy to treat solid tumors, such as EBV-positive lymphomas and EBV-positive nasopharyngeal carcinoma (see, e.g., Barker et al., 2010, Blood 116:5045-5049; Doubrovina et al., 2012, Blood 119:2644-2656; Prockop et al., 2016, J Clin Oncol 34:3012; and Gandhi et al., 2007, Am J Transplant 7:1293-1299).

Citation of a reference herein shall not be construed as an admission that such is prior art to the present disclosure.

3. SUMMARY OF THE INVENTION

In one aspect, provided herein is a method of treating a solid malignant tumor in a human patient comprising: (a) administering to the human patient a population of human cells comprising antigen-specific T cells that are specific for one or more antigens of the solid malignant tumor; and (b) informing the human patient about the potential risks for tumor flare depending on the anatomic site of the solid malignant tumor.

In another aspect, provided herein is a method of treating a solid malignant tumor in a human patient comprising: (a) administering to the human patient a population of human cells comprising antigen-specific T cells that are specific for one or more antigens of the solid malignant tumor; and (b) telling the human patient to contact his or her physician if tumor swelling occurs.

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops Waldeyer's ring lymphadenopathy; and (b) counseling the human patient to contact his or her physician if shortness of breath or stridor occurs.

In another aspect, provided herein is a method of treating a solid malignant tumor in a human patient comprising: (a) administering to the human patient a population of human cells comprising antigen-specific T cells that are specific for one or more antigens of the solid malignant tumor; (b) grading tumor flare in the human patient as Grade 1, 2, 3, 4, or 5 according to the Evaluation column in Table 1; and (c) managing tumor flare in the human patient according to the Intervention column in Table 1.

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops tumor flare that is Grade 2 tumor flare; and (b) treating the tumor flare medically. In certain embodiments, the method further comprises before step (b) a step of grading the tumor flare in the human patient as Grade 2 tumor flare. In a specific embodiment, Grade 2 tumor flare is tumor flare that is symptomatic with medical intervention indicated, but with no stridor or respiratory distress or hospitalization indicated, and no life-threatening airway compromise or urgent intervention indicated. In a specific embodiment, the step of treating the tumor flare medically comprises providing one or more pain medications to the human patient. In another specific embodiment, the solid malignant tumor is a necrotic tumor and the step of treating the tumor flare medically comprises providing one or more antibiotics to the human patient. In another specific embodiment, the solid malignant tumor is a necrotic tumor and the step of treating the tumor flare medically comprises providing one or more antibiotics to the human patient and providing one or more pain medications to the human patient.

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops tumor flare that is Grade 3 tumor flare; and (b) hospitalizing the human patient and monitoring the human patient as appropriate for the anatomic tumor site. In certain embodiments, the method further comprises before step (b) a step of grading the tumor flare in the human patient as Grade 3 tumor flare. In a specific embodiment, Grade 3 tumor flare is tumor flare with stridor or respiratory distress, or with hospitalization indicated, but with no life-threatening airway compromise or urgent intervention indicated.

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops tumor flare that is Grade 4 tumor flare; and (b) intubating the human patient to protect the airway or performing another intervention according to the anatomic tumor site. In certain embodiments, the method further comprises before step (b) a step of grading the tumor flare in the human patient as Grade 4 tumor flare. In a specific embodiment, Grade 4 tumor flare is tumor flare with life-threatening airway compromise or urgent intervention indicated.

In certain embodiments of the methods of treating described above, the administering step is by bolus intravenous infusion.

In specific embodiments, the administering step comprises administering at least about $1 \times 10^5$ cells of the population of human cells comprising antigen-specific T cells per kg per dose per week to the human patient. In specific embodiments, the administering step comprises administering at least about $1 \times 10^6$ cells to about $5 \times 10^6$ cells of the population of human cells comprising antigen-specific T cells per kg per dose per week to the human patient. In a specific embodiment, the administering step comprises administering at least about $2 \times 10^6$ cells of the population of human cells comprising antigen-specific T cells per kg per dose per week to the human patient.

In specific embodiments, the administering step comprises administering to the human patient at least two cycles of one dose per week of the population of human cells comprising antigen-specific T cells for at least two consecutive weeks, each cycle separated by a washout period during which no dose of the population of human cells comprising antigen-specific T cells is administered. In specific embodiments, the washout period is about 2, 3, or 4 weeks.

In another aspect, provided herein is a method of improving safety in treatment of a solid malignant tumor in a human patient with a population of human cells comprising antigen-specific T cells that are specific for one or more antigens of the solid malignant tumor, the method comprises informing the human patient about the potential risks of said treatment for tumor flare depending on the anatomic site of the solid malignant tumor.

In various embodiments, a method described above further comprises stopping treatment of the human patient with the population of human cells at the first indication of tumor flare.

In a specific embodiment of a method described above, the solid malignant tumor is nasopharyngeal carcinoma, gastric cancer, or leiomyosarcoma.

In a specific embodiments of a method described above, the solid malignant tumor described above is a lymphoproliferative disorder (LPD). In a specific embodiment, the LPD is a lymphoma. In a specific embodiment, the lymphoma is diffuse large B-cell lymphoma (DLBCL). In another specific embodiment, the lymphoma is plasmablastic lymphoma (PBL). In a particular embodiment, the LPD is Epstein-Barr virus (EBV)-positive LPD and the one or more antigens are one or more antigens of EBV. In some embodiments, the human patient is HIV-infected. In other embodiments, the human patient is a recipient of an hematopoietic stem cell transplant (HSCT). In other embodiments, the human patient is a recipient of a solid organ transplant (SOT). In some embodiments, the anatomic site of the solid malignant tumor is inside the lymph nodes. In other embodiments, the anatomic site of the solid malignant tumor is outside the lymph nodes.

In a specific embodiment of a method described above, the anatomic site of the solid malignant tumor is within the head and neck region. In a specific embodiment, the anatomic site of the solid malignant tumor is within the neck. In a specific embodiment, the anatomic site of the solid malignant tumor is inside the neck lymph nodes. In a further specific embodiment, the anatomic site of the solid malignant tumor is inside the left neck lymph nodes. In a particular embodiment, the anatomic site of the solid malignant tumor is inside the left neck lymph nodes at levels 2, 3 and 5.

In a specific embodiment of a method described above, the antigen-specific T cells are restricted by an HLA allele shared with the tumor cells in the human patient.

In a specific embodiment of a method described above, the antigen-specific T cells share at least 2 out of 10 HLA alleles with the tumor cells in the human patient (for example, two HLA-A alleles, two HLA-B alleles, two HLA-C alleles, two HLA-DRB1 alleles, and two HLA-DQB1 alleles).

In a specific embodiment of a method described above, the population of human cells comprising antigen-specific T cells is derived from a human donor that is allogeneic to the human patient.

In a specific embodiment of a method described above, the population of human cells comprising antigen-specific T cells contains at least 70% CD3$^+$ cells.

In a specific embodiment, the population of human cells comprising antigen-specific T cells described herein contains less than 500 alloreactive cytotoxic T lymphocyte precursors (CTLps) per million cells, when the amount of alloreactive CTLps per million cells is determined to be the average amount of alloreactive CTLps per million cells determined in N limiting dilution assays, each assay using a different population of target antigen presenting cells that are completely HLA-mismatched at low resolution relative to the population of human cells, wherein each different population of target antigen presenting cells is of different HLA type and does not present the one or more antigens of the solid malignant tumor, and wherein N is an integer greater than 1.

In another aspect, provided herein is the following: in a method of treating a solid malignant tumor in a human patient that comprises administering to the human patient a population of human cells comprising antigen-specific T cells that are specific for one or more antigens of the solid malignant tumor, wherein the improvement comprises informing the human patient about the potential risks for tumor flare depending on the anatomic site of the solid malignant tumor.

In another aspect, provided herein is the following: in a method of treating a solid malignant tumor in a human patient that comprises administering to the human patient a population of human cells comprising antigen-specific T cells that are specific for one or more antigens of the solid malignant tumor, wherein the improvement comprises telling the human patient to contact his or her physician if tumor swelling occurs.

In another aspect, provided herein is the following: in a method of treating a solid malignant tumor in a human patient that comprises administering to the human patient a population of human cells comprising antigen-specific T cells that are specific for one or more antigens of the solid malignant tumor, wherein the improvement comprises, wherein after said administering the human patient develops Waldeyer's ring lymphadenopathy, counseling the human patient to contact his or her physician if shortness of breath or stridor occurs.

In another aspect, provided herein is the following: in a method of treating a solid malignant tumor in a human patient that comprises administering to the human patient a population of human cells comprising antigen-specific T cells that are specific for one or more antigens of the solid malignant tumor, wherein the improvement comprises: (a) grading tumor flare in the human patient as Grade 1, 2, 3, 4, or 5 according to the Evaluation column in Table 1; and (b) managing tumor flare in the human patient according to the Intervention column in Table 1.

In another aspect, provided herein is the following: in a method of treating a solid malignant tumor in a human patient that comprises administering to the human patient a population of human cells comprising antigen-specific T cells that are specific for one or more antigens of the solid malignant tumor, wherein the improvement comprises, wherein after the administering the human patient develops tumor flare that is Grade 2 tumor flare, treating the tumor flare medically. In certain embodiments, the improvement further comprises before the step of treating the tumor flare medically a step of grading the tumor flare in the human patient as Grade 2 tumor flare. In a specific embodiment, Grade 2 tumor flare is tumor flare that is symptomatic with medical intervention indicated, but with no stridor or respiratory distress or hospitalization indicated, and no life-threatening airway compromise or urgent intervention indicated. In a specific embodiment, the step of treating the tumor flare medically comprises providing one or more pain medications to the human patient. In another specific embodiment, the solid malignant tumor is a necrotic tumor and the step of treating the tumor flare medically comprises providing one or more antibiotics to the human patient. In another specific embodiment, the solid malignant tumor is a necrotic tumor and the step of treating the tumor flare medically comprises providing one or more antibiotics to the human patient and providing one or more pain medications to the human patient.

In another aspect, provided herein is the following: in a method of treating a solid malignant tumor in a human patient that comprises administering to the human patient a population of human cells comprising antigen-specific T cells that are specific for one or more antigens of the solid malignant tumor, wherein the improvement comprises, wherein after the administering the human patient develops tumor flare that is Grade 3 tumor flare, hospitalizing the human patient and monitoring the human patient as appropriate for the anatomic tumor site. In certain embodiments, the improvement further comprises before the step of hospitalizing a step of grading the tumor flare in the human patient as Grade 3 tumor flare. In a specific embodiment, Grade 3 tumor flare is tumor flare with stridor or respiratory distress, or with hospitalization indicated, but with no life-threatening airway compromise or urgent intervention indicated.

In another aspect, provided herein is the following: in a method of treating a solid malignant tumor in a human patient that comprises administering to the human patient a population of human cells comprising antigen-specific T cells that are specific for one or more antigens of the solid malignant tumor, wherein the improvement comprises, wherein after the administering the human patient develops tumor flare that is Grade 4 tumor flare, intubating the human patient to protect the airway or performing another intervention according to the anatomic tumor site. In certain embodiments, the improvement further comprises before the step of intubating a step of grading the tumor flare in the human patient as Grade 4 tumor flare. In a specific embodiment, Grade 4 tumor flare is tumor flare with life-threatening airway compromise or urgent intervention indicated.

4. BRIEF DESCRIPTION OF FIGURE

FIGS. 1A-1F. Images of Lymphoma and Tumor Flare in a Patient Treated with EBV-Cytotoxic T Lymphocytes (CTLs). (A) Day 1 of treatment cycle with EBV-specific CTLs. The first dose of EBV-CTLs was infused on Day 1. Neck area mass measured 10 cm×8 cm×5 cm. There was no erythema. Chem 10 test result was within normal limits. Lactate dehydrogenase (LDH) level was 226 U/L. EBV DNA was 20,044 copies/mL. (B) Day 4 of treatment cycle with EBV-specific CTLs. Neck area mass measured 10 cm×8 cm×7 cm. Erythema (diffuse neck erythema) appeared and the patient experienced pain in the area. Chem 10 test result was within normal limits. LDH level was 467 U/L. (C) Day 8 of treatment cycle with EBV-specific CTLs. The second dose of EBV-CTLs was infused seven days after the first dose. Neck area mass measured 9 cm×8 cm×4 cm, and was soft. There was some erythema. New central necrosis appeared with skin breakdown. Chem 10 test result was within normal limits. LDH level was 446 U/L. EBV DNA was 244,132 copies/mL. (D) Day 8 of treatment cycle with EBV-specific CTLs. Neck area mass measured 11 cm×10 cm×4 cm, and was firm, erythematous and warm. Edema extended to anterior neck. Airway was clear. The patient was admitted for observation. Chem 10 test result was within normal limits. LDH level was 403 U/L. (E) Day 15 of treatment cycle with EBV-specific CTLs. The third dose of EBV-CTLs was infused seven days after the second dose. Neck area mass measured 10 cm×10 cm×4 cm and was soft and well-circumscribed. Necrosis was controlled. The patient experienced less pain in the area. There was serosanguinous drainage. Chem 10 test result was within normal limits. LDH level was 310 U/L. (F) Day 18 of treatment cycle with EBV-specific CTLs. Neck area mass measured 10 cm×10 cm×4 cm and was well-circumscribed. Necrosis was under better control. No drainage occurred. Chem 10 test result was within normal limits. LDH level was 298 U/L.

5. DETAILED DESCRIPTION

The present invention provides methods of treating a solid malignant tumor using antigen-specific T cells and methods of managing tumor flare in treatment of a solid malignant tumor using antigen-specific T cells. The methods provided herein improve the safety of treatment by informing the patient about the potential risks for tumor flare, telling the patient to contact his or her physician if tumor swelling occurs, counseling a patient with Waldeyer's ring lymph-adenopathy to contact his or her physician if shortness of breath or stridor occurs, or grading and managing tumor flare developed in the patient.

5.1. Methods of Treating Tumors Using Antigen-Specific T Cells and Methods of Improving Safety in Treatment of Tumors According to the invention, a patient whose solid malignant tumor is being treated with antigen-specific T cells may have a clinical reaction to the treatment that is manifested as swelling of the tumor. Such a reaction is called tumor flare. Other indications of tumor flare include, but are not limited to, pain at the tumor site, inflammation at the tumor site, fever, rash, and lymphocytosis. Tumor flare may cause risks to patients that vary depending at least partly on the anatomic site of the solid malignant tumor, the age of the patient and the condition of the patient. For example, if the solid malignant tumor being treated is within the neck, the tumor flare may cause stridor, respiratory distress, life-threatening airway compromise, or even death.

In one aspect, provided herein is a method of treating a solid malignant tumor in a human patient comprising: (a) administering to the human patient a population of human cells comprising antigen-specific T cells that are specific for one or more antigens of the solid malignant tumor; and (b) informing the human patient about the potential risks for tumor flare depending on the anatomic site of the solid malignant tumor.

In another aspect, provided herein is a method of treating a solid malignant tumor in a human patient comprising: (a) administering to the human patient a population of human cells comprising antigen-specific T cells that are specific for one or more antigens of the solid malignant tumor; and (b) telling the human patient to contact his or her physician if tumor swelling occurs.

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops Waldeyer's ring lymphadenopathy; and (b) counseling the human patient to contact his or her physician if shortness of breath or stridor occurs.

In another aspect, provided herein is a method of treating a solid malignant tumor in a human patient comprising: (a) administering to the human patient a population of human cells comprising antigen-specific T cells that are specific for one or more antigens of the solid malignant tumor; (b) grading tumor flare in the human patient as Grade 1, 2, 3, 4, or 5 according to the Evaluation column in Table 1; and (c) managing tumor flare in the human patient according to the Intervention column in Table 1.

TABLE 1

Severity Grading and Suggested Management of Tumor Flare.

| Tumor Flare Severity | Evaluation | Intervention |
|---|---|---|
| Grade 1 | Asymptomatic, clinical or diagnostic observations only | No intervention |
| Grade 2 | Symptomatic; medical intervention indicated | Medical treatment (e.g., pain medication; antibiotics for necrotic tumor) |
| Grade 3 | Stridor, respiratory distress; hospitalization indicated | Hospitalization with monitoring as appropriate for the anatomic tumor site |
| Grade 4 | Life-threatening airway compromise; urgent intervention indicated | Intubation to protect the airway if appropriate; other intervention according to the anatomic tumor site |
| Grade 5 | Death | — |

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops tumor flare that is Grade 2 tumor flare; and (b) treating the tumor flare medically. In certain embodiments, the method further comprises before step (b) a step of grading the tumor flare in the human patient as Grade 2 tumor flare. In a specific embodiment, Grade 2 tumor flare is tumor flare that is symptomatic with medical intervention indicated, but with no stridor or respiratory distress or hospitalization indicated, and no life-threatening airway compromise or urgent intervention indicated. In a specific embodiment, the step of treating the Grade 2 tumor flare medically comprises providing one or more pain medications to the human patient. In another specific embodiment, the solid malignant tumor is a necrotic tumor and the step of treating the Grade 2 tumor flare medically comprises providing one or more antibiotics to the human patient. In another specific embodiment, the solid malignant tumor is a necrotic tumor and the step of treating the Grade 2 tumor flare medically comprises providing one or more antibiotics to the human patient and providing one or more pain medications to the human patient.

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops tumor flare that is Grade 3 tumor flare; and (b) hospitalizing the human patient and monitoring the human patient as appropriate for the anatomic tumor site. In certain embodiments, the method further comprises before step (b) a step of grading the tumor flare in the human patient as Grade 3 tumor flare. In a specific embodiment, Grade 3 tumor flare is tumor flare with stridor or respiratory distress, or with hospitalization indicated, but with no life-threatening airway compromise or urgent intervention indicated. In specific embodiments, hospitalizing the human patient comprises treating the Grade 3 tumor flare medically. In a specific embodiment, the step of treating the Grade 3 tumor flare medically comprises providing one or more pain medications to the human patient. In another specific embodiment, the solid malignant tumor is a necrotic tumor and the step of treating the Grade 3 tumor flare medically comprises providing one or more antibiotics to the human patient. In another specific embodiment, the solid malignant tumor is a necrotic tumor and the step of treating the Grade 3 tumor flare medically comprises providing one or more antibiotics to the human patient and providing one or more pain medications to the human patient.

In another aspect, provided herein is a method of treating a solid malignant tumor in a human patient comprising: (a) administering to the human patient a population of human cells comprising antigen-specific T cells that are specific for one or more antigens of the solid malignant tumor, wherein after the administering the human patient develops tumor flare that is Grade 4 tumor flare; and (b) intubating the human patient to protect the airway or performing another intervention according to the anatomic tumor site. In certain embodiments, the method further comprises before step (b) a step of grading the tumor flare in the human patient as Grade 4 tumor flare. In a specific embodiment, Grade 4 tumor flare is tumor flare with life-threatening airway compromise or urgent intervention indicated. In various embodiments, the method further comprises hospitalizing the human patient and monitoring the human patient as appropriate for the anatomic tumor site. In specific embodiments, hospitalizing the human patient comprises treating the Grade 4 tumor flare medically. In a specific embodiment, the step of treating the Grade 4 tumor flare medically comprises providing one or more pain medications to the human patient. In another specific embodiment, the solid malignant tumor is a necrotic tumor and the step of treating the Grade 4 tumor flare medically comprises providing one or more antibiotics to the human patient. In another specific embodiment, the solid malignant tumor is a necrotic tumor and the step of treating the Grade 4 tumor flare medically comprises providing one or more antibiotics to the human patient and providing one or more pain medications to the human patient.

In another aspect, provided herein is a method of treating a solid malignant tumor in a human patient comprising: (a) administering to the human patient a population of human cells comprising antigen-specific T cells that are specific for one or more antigens of the solid malignant tumor; and (b) monitoring the human patient for indication of tumor flare.

In another aspect, provided herein is a method of improving safety in treatment of a solid malignant tumor in a human patient with a population of human cells comprising antigen-specific T cells that are specific for one or more antigens of the solid malignant tumor, the method comprises informing the human patient about the potential risks of said treatment for tumor flare depending on the anatomic site of the solid malignant tumor.

In another aspect, provided herein is a method of treating a solid malignant tumor in a human patient with a population of human cells comprising antigen-specific T cells that are specific for one or more antigens of the solid malignant tumor, the method comprising monitoring the human patient for an indication of tumor flare.

Another aspect provides: in a method of treating a solid malignant tumor in a human patient that comprises administering to the human patient a population of human cells comprising antigen-specific T cells that are specific for one or more antigens of the solid malignant tumor, wherein the improvement comprises informing the human patient about the potential risks for tumor flare depending on the anatomic site of the solid malignant tumor.

Another aspect provides: in a method of treating a solid malignant tumor in a human patient that comprises administering to the human patient a population of human cells comprising antigen-specific T cells that are specific for one or more antigens of the solid malignant tumor, wherein the improvement comprises telling the human patient to contact his or her physician if tumor swelling occurs.

Another aspect provides: in a method of treating a solid malignant tumor in a human patient that comprises administering to the human patient a population of human cells comprising antigen-specific T cells that are specific for one or more antigens of the solid malignant tumor, wherein the improvement comprises, wherein after said administering the human patient develops Waldeyer's ring lymphadenopathy, counseling the human patient to contact his or her physician if shortness of breath or stridor occurs.

Another aspect provides: in a method of treating a solid malignant tumor in a human patient that comprises administering to the human patient a population of human cells comprising antigen-specific T cells that are specific for one or more antigens of the solid malignant tumor, wherein the improvement comprises: (a) grading tumor flare in the human patient as Grade 1, 2, 3, 4, or 5 according to the Evaluation column in Table 1; and (b) managing tumor flare in the human patient according to the Intervention column in Table 1.

Another aspect provides: in a method of treating a solid malignant tumor in a human patient that comprises administering to the human patient a population of human cells comprising antigen-specific T cells that are specific for one or more antigens of the solid malignant tumor, wherein the improvement comprises, wherein after the administering the human patient develops tumor flare that is Grade 2 tumor flare, treating the tumor flare medically. In certain embodiments, the improvement further comprises before the step of treating the tumor flare medically a step of grading the tumor flare in the human patient as Grade 2 tumor flare. In a specific embodiment, Grade 2 tumor flare is tumor flare that is symptomatic with medical intervention indicated, but with no stridor or respiratory distress or hospitalization indicated, and no life-threatening airway compromise or urgent intervention indicated. In a specific embodiment, the step of treating the Grade 2 tumor flare medically comprises providing one or more pain medications to the human patient. In another specific embodiment, the solid malignant tumor is a necrotic tumor and the step of treating the Grade 2 tumor flare medically comprises providing one or more antibiotics to the human patient. In another specific embodiment, the solid malignant tumor is a necrotic tumor and the step of treating the Grade 2 tumor flare medically comprises providing one or more antibiotics to the human patient and providing one or more pain medications to the human patient.

Another aspect provides: in a method of treating a solid malignant tumor in a human patient that comprises administering to the human patient a population of human cells comprising antigen-specific T cells that are specific for one or more antigens of the solid malignant tumor, wherein the improvement comprises, wherein after the administering the human patient develops tumor flare that is Grade 3 tumor flare, hospitalizing the human patient and monitoring the human patient as appropriate for the anatomic tumor site. In certain embodiments, the improvement further comprises before the step of hospitalizing a step of grading the tumor flare in the human patient as Grade 3 tumor flare. In a specific embodiment, Grade 3 tumor flare is tumor flare with stridor or respiratory distress, or with hospitalization indicated, but with no life-threatening airway compromise or urgent intervention indicated. In specific embodiments, hospitalizing the human patient comprises treating the Grade 3 tumor flare medically. In a specific embodiment, the step of treating the Grade 3 tumor flare medically comprises providing one or more pain medications to the human patient. In another specific embodiment, the solid malignant tumor is a necrotic tumor and the step of treating the Grade 3 tumor flare medically comprises providing one or more antibiotics to the human patient. In another specific embodiment, the solid malignant tumor is a necrotic tumor and the step of treating the Grade 3 tumor flare medically comprises providing one or more antibiotics to the human patient and providing one or more pain medications to the human patient.

Another aspect provides: in a method of treating a solid malignant tumor in a human patient that comprises administering to the human patient a population of human cells comprising antigen-specific T cells that are specific for one or more antigens of the solid malignant tumor, wherein the improvement comprises, wherein after the administering the human patient develops tumor flare that is Grade 4 tumor flare, intubating the human patient to protect the airway or performing another intervention according to the anatomic tumor site. In certain embodiments, the improvement further comprises before the step of intubating a step of grading the tumor flare in the human patient as Grade 4 tumor flare. In a specific embodiment, Grade 4 tumor flare is tumor flare with life-threatening airway compromise or urgent intervention indicated. In various embodiments, the improvement further comprises hospitalizing the human patient and monitoring the human patient as appropriate for the anatomic tumor site. In specific embodiments, hospitalizing the human patient comprises treating the Grade 4 tumor flare medically. In a specific embodiment, the step of treating the Grade 4 tumor flare medically comprises providing one or more pain medications to the human patient. In another specific embodiment, the solid malignant tumor is a necrotic tumor and the step of treating the Grade 4 tumor flare medically comprises providing one or more antibiotics to the human patient. In another specific embodiment, the solid malignant tumor is a necrotic tumor and the step of treating the Grade 4 tumor flare medically comprises providing one or more antibiotics to the human patient and providing one or more pain medications to the human patient.

In a specific embodiment, the grade of tumor flare is determined according to the latest applicable National Cancer Institute Common Terminology Criteria for Adverse Events (NCI CTCAE).

The pain medication that can be provided to the human patient with tumor flare, according to certain embodiments of the methods described herein, can be any medication known in the art that can be used for relieving pain. Non-limiting exemplary pain medications that can be provided to the human patient include acetaminophen, non-steroidal anti-inflammatory drugs (NSAIDs) (such as, for example, aspirin, naproxen, ibuprofen, fenoprofen, flurbiprofen, ketoprofen, oxaprozin, diclofenac sodium, etodolac, indomethacin, ketorolac, sulindac, tolmetin, meclofenamate, mefenamic acid, nabumetone, piroxicam, and cyclo-oxygenase-2 (COX-2) inhibitors such as celecoxib), and narcotics (such as, for example, morphine, oxycodone, hydromorphone, meperidine, oxymorphone, fentanyl, and methadone). The pain medication can be administered systemically (e.g., orally) or locally at the site of pain. In a specific embodiment, the pain medication provided to the human patient is hydromorphone. The selection of the pain medication(s), the route of its administration, and the amount to be administered to the human patient preferably are determined by the physician, and can be determined, for example, based on the site of the solid malignant tumor, the level of pain experienced by the human patient, the condition of the human patient and the knowledge of the physician. In addition to or in lieu of providing one or more pain medications to the human patient, a non-medication pain relief method can be performed in the step of treating the tumor flare medically, such as, for example, a cold therapy or acupuncture.

The antibiotic that can be provided to the human patient having tumor flare and a necrotic tumor, according to certain embodiments of the methods described herein, can be any antibiotic known in the art that can be used for preventing and/or treating infections associated with tumor necrosis. Non-limiting exemplary antibiotics that can be provided to the human patient include, penicillins (such as penicillin or amoxicillin), cephalosporins (such as cephalexin), macrolides (such as erythromycin, clarithromycin, or azithromycin), fluoroquinolones (such as ciprofloxacin, levofloxacin, or ofloxacin), sulfonamides (such as co-trimoxazole or trimethoprim), tetracyclines (such as tetracycline or doxycycline), and aminoglycosides (such as gentamicin or tobramycin). The antibiotic can be administered systemically (e.g., orally), or can be applied directly to an open wound at the site of tumor necrosis. The selection of the antibiotic(s), the route of its administration, and the amount to be administered to the human patient preferably are determined by the physician, and can be determined, for example, based on the site of the solid malignant tumor, the severity of tumor necrosis, the condition of the human patient and the knowledge of the physician. If the necrotic tumor has caused an open wound, a wound dressing can be applied to the open wound in addition to or in lieu of providing one or more antibiotics to the human patient.

In a specific embodiment of the methods described herein, the method further comprises stopping treatment with the population of human cells at the first indication of tumor flare. In another specific embodiment of the methods described herein, the method further comprises stopping treatment with the population of human cells when the tumor flare is life-threatening or deemed an excessive risk by the treating physician. The human patient may be further monitored for grading and managing tumor flare after treatment with the population of human cells is stopped. In one embodiment, where tumor flare subsides or decreases after stopping treatment, treatment may be re-initiated, preferably with appropriate monitoring and depending on the severity of the tumor flare and risk/benefit assessment of the immediately prior treatment with the population of human cells.

5.1.1. Administration and Dosage of the Population of Human Cells

The route of administration of the population of human cells comprising antigen-specific T cells and the amount to be administered to the human patient can be determined based on the nature of the tumor, condition of the human patient and the knowledge of the physician. Generally, the administration of the population of human cells is intravenous. In certain embodiments, the method of treating comprises infusing to the human patient the population of human cells comprising antigen-specific T cells. In specific embodiments, the infusing is by bolus intravenous infusion.

In specific embodiments, the method described herein comprises administering to the human patient the population of human cells comprising antigen-specific T cells, at a dose that is at least $1 \times 10^2$ cells of the population of human cells comprising antigen-specific T cells per kg of the human patient. In specific embodiments, the method described herein comprises administering to the human patient the population of human cells comprising antigen-specific T cells, at a dose that is at least $1 \times 10^3$ cells of the population of human cells comprising antigen-specific T cells per kg of the human patient. In specific embodiments, the method described herein comprises administering to the human patient the population of human cells comprising antigen-specific T cells, at a dose that is at least $1 \times 10^4$ cells of the population of human cells comprising antigen-specific T cells per kg of the human patient. In specific embodiments, the method described herein comprises administering to the human patient the population of human cells comprising antigen-specific T cells, at a dose that is at least $1 \times 10^5$ cells of the population of human cells comprising antigen-specific T cells per kg of the human patient. In a specific embodiment, the method of treating comprises administering to the human patient the population of human cells comprising antigen-specific T cells, at a dose that is about $1 \times 10^2$ cells of the population of human cells comprising antigen-specific T cells per kg of the human patient. In another specific embodiment, the method of treating comprises administering to the human patient the population of human cells comprising antigen-specific T cells, at a dose that is about $5 \times 10^2$ cells of the population of human cells comprising antigen-specific T cells per kg of the human patient. In another specific embodiment, the method of treating comprises administering to the human patient the population of human cells comprising antigen-specific T cells, at a dose that is about $1 \times 10^3$ cells of the population of human cells comprising antigen-specific T cells per kg of the human patient. In another specific embodiment, the method of treating comprises administering to the human patient the population of human cells comprising antigen-specific T cells, at a dose that is about $5 \times 10^3$ cells of the population of human cells comprising antigen-specific T cells per kg of the human patient. In another specific embodiment, the method of treating comprises administering to the human patient the population of human cells comprising antigen-specific T cells, at a dose that is about $1 \times 10^4$ cells of the population of human cells comprising antigen-specific T cells per kg of the human patient. In another specific embodiment, the method of treating comprises administering to the human patient the population of human cells comprising antigen-specific T cells, at a dose that is about $5\times10^4$ cells of the population of human cells comprising antigen-specific T cells per kg of the human patient. In another specific embodiment, the method of treating comprises administering to the human patient the population of human cells comprising antigen-specific T cells, at a dose that is about $5\times10^5$ cells of the population of human cells comprising antigen-specific T cells per kg of the human patient. In another specific embodiment, the method of treating comprises administering to the human patient the population of human cells comprising antigen-specific T cells, at a dose that is about $1\times10^6$ cells of the population of human cells comprising antigen-specific T cells per kg of the human patient. In another specific embodiment, the method of treating comprises administering to the human patient the population of human cells comprising antigen-specific T cells, at a dose that is about $2\times10^6$ cells of the population of human cells comprising antigen-specific T cells per kg of the human patient. In another specific embodiment, the method of treating comprises administering to the human patient the population of human cells comprising antigen-specific T cells, at a dose that is about $3\times10^6$ cells of the population of human cells comprising antigen-specific T cells per kg of the human patient. In another specific embodiment, the method of treating comprises administering to the human patient the population of human cells comprising antigen-specific T cells, at a dose that is about $4\times10^6$ cells of the population of human cells comprising antigen-specific T cells per kg of the human patient. In another specific embodiment, the method of treating comprises administering to the human patient the population of human cells comprising antigen-specific T cells, at a dose that is about $5\times10^6$ cells of the population of human cells comprising antigen-specific T cells per kg of the human patient. In another specific embodiment, the method of treating comprises administering to the human patient the population of human cells comprising antigen-specific T cells, at a dose that is about $6\times10^6$ cells of the population of human cells comprising antigen-specific T cells per kg of the human patient. In another specific embodiment, the method of treating comprises administering to the human patient the population of human cells comprising antigen-specific T cells, at a dose that is about $1\times10^7$ cells of the population of human cells comprising antigen-specific T cells per kg of the human patient. In another specific embodiment, the method of treating comprises administering to the human patient the population of human cells comprising antigen-specific T cells, at a dose that is about $1\times10^2$ to $5\times10^2$ cells of the population of human cells comprising antigen-specific T cells per kg of the human patient. In another specific embodiment, the method of treating comprises administering to the human patient the population of human cells comprising antigen-specific T cells, at a dose that is about $5\times10^2$ to $1\times10^3$ cells of the population of human cells comprising antigen-specific T cells per kg of the human patient. In another specific embodiment, the method of treating comprises administering to the human patient the population of human cells comprising antigen-specific T cells, at a dose that is about $1\times10^3$ to $5\times10^3$ cells of the population of human cells comprising antigen-specific T cells per kg of the human patient. In another specific embodiment, the method of treating comprises administering to the human patient the population of human cells comprising antigen-specific T cells, at a dose that is about $5\times10^3$ to $1\times10^4$ cells of human cells comprising antigen-specific T cells per kg of the human patient. In another specific embodiment, the method of treating comprises administering to the human patient the population of human cells comprising antigen-specific T cells, at a dose that is about $1\times10^4$ to $5\times10^4$ cells of the population of human cells comprising antigen-specific T cells per kg of the human patient. In another specific embodiment, the method of treating comprises administering to the human patient the population of human cells comprising antigen-specific T cells, at a dose that is about $5\times10^4$ to $1\times10^5$ cells of the population of human cells comprising antigen-specific T cells per kg of the human patient. In another specific embodiment, the method of treating comprises administering to the human patient the population of human cells comprising antigen-specific T cells, at a dose that is about $1\times10^5$ to $5\times10^5$ cells of the population of human cells comprising antigen-specific T cells per kg of the human patient. In another specific embodiment, the method of treating comprises administering to the human patient the population of human cells comprising antigen-specific T cells, at a dose that is about $5\times10^5$ to $1\times10^6$ cells of the population of human cells comprising antigen-specific T cells per kg of the human patient. In another specific embodiment, the method of treating comprises administering to the human patient the population of human cells comprising antigen-specific T cells, at a dose that is about $1\times10^6$ to $5\times10^6$ cells of the population of human cells comprising antigen-specific T cells per kg of the human patient. In another specific embodiment, the method of treating comprises administering to the human patient the population of human cells comprising antigen-specific T cells, at a dose that is about $1\times10^6$ to $2\times10^6$ cells of the population of human cells comprising antigen-specific T cells per kg of the human patient. In another specific embodiment, the method of treating comprises administering to the human patient the population of human cells comprising antigen-specific T cells, at a dose that is about $2\times10^6$ to $5\times10^6$ cells of the population of human cells comprising antigen-specific T cells per kg of the human patient. In another specific embodiment, the method of treating comprises administering to the human patient the population of human cells comprising antigen-specific T cells, at a dose that is about $5\times10^6$ to $1\times10^7$ cells of the population of human cells comprising antigen-specific T cells per kg of the human patient.

In a preferred embodiment, the method of treating comprises administering to the human patient the population of human cells comprising antigen-specific T cells at the dose described above weekly. In a specific embodiment, the method of treating comprises administering to the human patient the population of human cells comprising antigen-specific T cells at the dose described above twice weekly. In another specific embodiment, the method of treating comprises administering to the human patient the population of human cells comprising antigen-specific T cells at the dose described above biweekly. In another specific embodiment, the method of treating comprises administering to the human patient the population of human cells comprising antigen-specific T cells at the dose described above every three weeks.

In certain embodiments, the method of treating comprises administering to the human patient at least 2 doses of the population of human cells comprising antigen-specific T cells. In specific embodiments, the method of treating comprises administering to the human patient 2, 3, 4, 5, or 6 doses of the population of human cells comprising antigen-specific T cells. In a specific embodiment, the method of treating comprises administering to the human patient 2 doses of the population of human cells comprising antigen-specific T cells. In another specific embodiment, the method of treating comprises administering to the human patient 3 doses of the population of human cells comprising antigen-specific T cells. In another specific embodiment, the method of treating comprises administering to the human patient 4 doses of the population of human cells comprising antigen-specific T cells.

In specific embodiments, the method of treating comprises administering to the human patient at least two cycles (e.g., 2, 3, 4, 5, or 6 cycles) of one dose per week of the population of human cells comprising antigen-specific T cells for at least two consecutive weeks (e.g., 2, 3, 4, 5, or 6 consecutive weeks), each cycle separated by a washout period during which no dose of the population of human cells comprising antigen-specific T cells is administered. In a specific embodiment, the at least two consecutive weeks are 2 consecutive weeks. In a preferred embodiment, the at least two consecutive weeks are 3 consecutive weeks. In another specific embodiment, the at least two consecutive weeks are 4 consecutive weeks. In another specific embodiment, the method of treating comprises administering to the human patient two, three, four, five, or six cycles of one dose per week of the population of human cells comprising antigen-specific T cells for three consecutive weeks, each cycle separated by a washout period during which no dose of the population of human cells comprising antigen-specific T cells is administered. In another specific embodiment, the method of treating comprises administering to the human patient a first cycle of one dose per week of the population of human cells comprising antigen-specific T cells for 3 consecutive weeks followed by a washout period during which no dose of the population of human cells comprising antigen-specific T cells is administered, followed by a second cycle of said one dose per week of the population of human cells comprising antigen-specific T cells for 3 consecutive weeks. In specific embodiments, the washout period is at least about 1 week (e.g., about 1-6 weeks). In specific embodiments, the washout period is about 1, 2, 3, or 4 weeks. In specific embodiments, the washout period is at least about 2 weeks (e.g., about 2-6 weeks). In specific embodiments, the washout period is about 2, 3, or 4 weeks. In a specific embodiment, the washout period is about 2 weeks. In a preferred embodiment, the washout period is about 3 weeks. In another specific embodiment, the washout period is about 4 weeks. In a specific embodiment, an additional cycle is administered only when the previous cycle has not exhibited toxicity (for example, no grade 3-5 serious adverse events, graded according to NCI CTCAE 4.0). Preferably, an additional cycle is administered only when no adverse event has occurred during and after the previous cycle (for example, no grade 3-5 serious adverse events, graded according to NCI CTCAE 4.0, and no Grade 3-5 tumor flare, graded according to Table 1). In a specific embodiment, wherein the human patient has Grade 2 tumor flare, an additional cycle is administered, for example, after the treating physician determines such is suitable after a risk/benefit assessment.

In specific embodiments, the method of treating comprises administering to the human patient continuously the population of human cells comprising antigen-specific T cells at a dose described herein weekly (i.e., there is no week during which the population of human cells comprising antigen-specific T cells is not administered, and thus there is no washout period).

In certain embodiments, a first dosage regimen described herein is carried out for a first period of time, followed by a second and different dosage regimen described herein that is carried out for a second period of time, wherein the first period of time and the second period of time are optionally separated by a washout period. In specific embodiments, the washout period is at least about 1 week (e.g., about 1-6 weeks). In specific embodiments, the washout period is about 1, 2, 3, or 4 weeks. In specific embodiments, the washout period is at least about 2 weeks (e.g., about 2-6 weeks). In specific embodiments, the washout period is about 2, 3, or 4 weeks. In a specific embodiment, the washout period is about 2 weeks. In a preferred embodiment, the washout period is about 3 weeks. In another specific embodiment, the washout period is about 4 weeks. In a specific embodiment, the second dosage regimen is carried out only when the first dosage regimen has not exhibited toxicity (for example, no grade 3-5 serious adverse events, graded according to NCI CTCAE 4.0). Preferably, the second dosage regimen is carried out only when no adverse event has occurred during and after the first dosage regimen (for example, no grade 3-5 serious adverse events, graded according to NCI CTCAE 4.0, and no grade 3-5 tumor flare, graded according to Table 1).

In specific embodiments, the administering of the population of human cells comprising antigen-specific T cells does not result in any graft-versus-host disease (GvHD) in the human patient.

As noted above, the term "about" shall be construed so as to allow normal variation, such as, for example, a variation within 20%.

5.1.2. Serial Treatment with Different Cell Populations

In certain embodiments, the method of treating a solid malignant tumor described above further comprises, after administering to the human patient a first population of human cells comprising antigen-specific T cells that are specific for one or more antigens of the solid malignant tumor, administering to the human patient a second population of human cells comprising antigen-specific T cells that are specific for one or more antigens of the solid malignant tumor, wherein the antigen-specific T cells in the second population of human cells are restricted by a different HLA allele (different from the HLA allele by which antigen-specific cells contained in the first population of human cells are restricted) shared with the tumor cells in the human patient. In a specific embodiment, the method of treating a solid malignant tumor described above comprises administering a first cycle of one dose per week of the first population of human cells comprising antigen-specific T cells, for at least two consecutive weeks (e.g., 2, 3, 4, 5, or 6 consecutive weeks), optionally followed by a washout period during which no dose of any population of human cells comprising antigen-specific T cells is administered, and followed by a second cycle of one dose per week of the second population of human cells comprising antigen-specific T cells for at least two consecutive weeks (e.g., 2, 3, 4, 5, or 6 consecutive weeks). In specific embodiments, the washout period is at least about 1 week (e.g., about 1-6 weeks). In specific embodiments, the washout period is about 1, 2, 3, or 4 weeks. In specific embodiments, the washout period is at least about 2 weeks (e.g., about 2-6 weeks). In specific embodiments, the washout period is about 2, 3, or 4 weeks. In a specific embodiment, the washout period is about 2 weeks. In a preferred embodiment, the washout period is about 3 weeks. In certain embodiments, the human patient has no response, an incomplete response, or a suboptimal response (i.e., the human patient may still have a substantial benefit from continuing treatment, but has reduced chances of optimal long-term outcomes) after administering the first population of human cells comprising antigen-specific T cells and prior to administering the second population of human cells comprising antigen-specific T cells.

The first and second populations of human cells comprising antigen-specific T cells can each be administered by any route and any dosage regimen as described in Section 5.1.1, supra.

In specific embodiments, two populations of human cells comprising antigen-specific T cells that are each restricted (i.e., antigen-specific T cells in the two populations of human cells are each restricted) by a different HLA allele shared with the tumor cells in the human patient are administered serially. In specific embodiments, three populations of human cells comprising antigen-specific T cells that are each restricted (i.e., antigen-specific T cells in the three populations of human cells are each restricted) by a different HLA allele shared with the tumor cells in the human patient are administered serially. In specific embodiments, four populations of human cells comprising antigen-specific T cells that are each restricted (i.e., antigen-specific T cells in the four populations of human cells are each restricted) by a different HLA allele shared with the tumor cells in the human patient are administered serially. In specific embodiments, more than four populations of human cells comprising antigen-specific T cells that are each restricted (i.e., antigen-specific T cells in the more than four populations of human cells are each restricted) by a different HLA allele shared with the tumor cells in the human patient are administered serially.

5.1.3. Additional Therapies and Previous Therapies

In specific embodiments, the human patient is concurrently treated with a second therapy for the solid malignant tumor (which second therapy is not treatment with a population of human cells comprising antigen-specific T cells according to the invention), for example, at about the same time, the same day, or same week, or same treatment period (treatment cycle) during which the population of human cells comprising antigen-specific T cells is administered, or on similar dosing schedules, or on different but overlapping dosing schedules. In specific embodiments, no second therapy for the solid malignant tumor is concurrently administered to the human patient over a period of time over which the population of human cells is repeatedly administered to the human patient. The second therapy can be any anti-cancer therapy known in the art (e.g., a chemotherapy, including a combination chemotherapy, or a radiotherapy).

In specific embodiments, the human patient has failed a previous therapy for the solid malignant tumor, which previous therapy is not treatment with a population of human cells comprising antigen-specific T cells according to the invention, due to resistance to or intolerance of the previous therapy. A disease is considered resistant to a therapy, if it has no response, or has an incomplete response (a response that is less than a complete remission), or progresses, or relapses after the therapy. The previous therapy can be an anti-cancer therapy known in the art (e.g., a chemotherapy, including a combination chemotherapy, or a radiotherapy).

Combination chemotherapy involves the therapeutic use over the same treatment period of two or more different chemotherapeutic agents to treat cancer. Exemplary combination chemotherapies that can be the second therapy or previous therapy described herein include, but are not limited to (the combinations being of the chemotherapeutic agents in parentheses): 7+3 (7 days of cytarabine plus 3 days of an anthracycline antibiotic, either daunorubicin or idarubicin), ABVD (doxorubicin, bleomycin, vinblastine, dacarbazine), BACOD (bleomycin, doxorubicin, cyclophosphamide, vincristine, dexamethasone), BEACOPP (bleomycin, etoposide, doxorubicin, cyclophosphamide, vincristine, procarbazine, prednisone), Dose-Escalated BEACOPP, CBV (cyclophosphamide, carmustine, etoposide), COP (cyclophosphamide, vincristine, and prednisone or prednisolone), CHOEP (cyclophosphamide, doxorubicin, etoposide, vincristine, prednisone), CEOP (cyclophosphamide, etoposide, vincristine, prednisone), CEPP (cyclophosphamide, etoposide, procarbazine, prednisone), ChlVPP (chlorambucil, vincristine, procarbazine, prednisone, etoposide, vinblastine, doxorubicin), CHOP (cyclophosphamide, doxorubicin, vincristine, prednisone), DCEP (dexamethasone, cyclophosphamide, etoposide, platinum agent), DHAP (dexamethasone, cytarabine, platinum agent), DICE (dexamethasone, ifosfamide, cisplatin, etoposide), DT-PACE (dexamethasone, thalidomide, platinum agent, doxorubicin, cyclophosphamide, etoposide), EPOCH (etoposide, prednisone, vincristine, cyclophosphamide, doxorubicin), DA-EPOCH (Dose-Adjusted EPOCH), ESHAP (etoposide, methylprednisolone, cytarabine, cisplatin), FCM (fludarabine, cyclophosphamide, mitoxantrone), FM (fludarabine, mitoxantrone), FLAG (fludarabine, cytarabine, G-CSF), FLAG-IDA (fludarabine, cytarabine, idarubicin, G-CSF), FLAG-MITO (mitoxantrone, fludarabine, cytarabine, G-CSF), FLAMSA (fludarabine, cytarabine, amsacrine), FLAMSA-BU (fludarabine, cytarabine, amsacrine, busulfan), FLAMSA-MEL (fludarabine, cytarabine, amsacrine, melphalan), GVD (gemcitabine, vinorelbine, pegylated liposomal doxorubicin), GEMOX (gemcitabine, oxaliplatin), IAC (idarubicin ×3 days plus cytarabine ×7 days), ICE (ifosfamide, carboplatin, etoposide), IVAC (etopside, cytarabine, ifosfamide), m-BACOD (methotrexate, bleomycin, doxorubicin, cyclophosphamide, vincristine, dexamethasone), MACOP-B (methotrexate, leucovorin, doxorubicin, cyclophosphamide, vincristine, prednisone, bleomycin), MINE (mesna, ifosfamide, novantrone, etoposide), MOPP (mechlorethamine, vincristine, procarbazine, prednisone), MVP (mitomycin, vindesine, cisplatin), PACE (platinum agent, doxorubicin, cyclophosphamide, etoposide), PEB (cisplatin, etoposide, bleomycin), POMP (6-mercaptopurine, vincristine, methotrexate, prednisone), ProMACE-MOPP (methotrexate, doxorubicin, cyclophosphamide, etoposide, mechlorethamine, vincristine, procarbazine, prednisone), ProMACE-CytaBOM (prednisone, doxorubicin, cyclophosphamide, etoposide, cytarabine, bleomycin, vincristine, methotrexate, leucovorin), RVD (lenalidomide, bortezomib, dexamethasone), Stanford V (doxorubicin, mechlorethamine, bleomycin, vinblastine, vincristine, etoposide, prednisone), Thal/Dex (thalidomide, dexamethasone), VAD (vincristine, doxorubicin, dexamethasone), VAMP (vincristine, amethopterin, 6-mercaptopurine and prednisone, or vincristine, doxorubicin, methotrexate and prednisone, or vincristine, doxorubicin and methylprednisolone), VAPEC-B (vincristine, doxorubicin, prednisone, etoposide, cyclophosphamide, bleomycin), VD-PACE (bortezomib, dexamethasone, platinum agent, doxorubicin, cyclophosphamide, etoposide), VTD-PACE (bortezomib, thalidomide, dexamethasone, platinum agent, doxorubicin, cyclophosphamide, etoposide), DA-REPOCH (rituximab, etoposide, prednisolone, vincristine, cyclophosphamide, hydroxydaunorubicin), RIVAC (rituximab, ifosphamide, etoposide, cytarabine), and RGDP (rituximab, gemcitabine, dexamethasone, cisplatin).

Radiation therapies use high-energy radiation to kill cancer cells by damaging their DNA. Exemplary radiation therapies that can be the second therapy or previous therapy described herein include, but are not limited to conventional external beam radiation therapy, stereotactic radiation therapy, intensity-modulated radiation therapy, volumetric modulated arc therapy, particle therapy, auger therapy, brachytherapy, and radioisotope therapy.

5.2. Generation of the Population of Human Cells Comprising Antigen-Specific T Cells The population of human cells comprising antigen-specific T cells use for treating the human patient can be generated as described herein.

5.2.1. Ex Vivo Sensitized Antigen-Specific T Cells

In some embodiments, the population of human cells comprising antigen-specific T cells are generated by ex vivo sensitizing human T cells to one or more antigens of the solid malignant tumor, said ex vivo sensitizing comprises co-culturing, over a period of time in culture, a population of human blood cells comprising the human T cells with antigen presenting cells presenting the one or more antigens. In a preferred embodiment, the ex vivo sensitizing results in expansion of antigen-specific T cells that are specific for the one or more antigens. In a specific embodiment, the human T cells that are ex vivo sensitized are not genetically engineered to be specific for the one or more antigens (e.g., by expression of a chimeric antigen receptor (CAR) or T cell receptor (TCR) specific to the one or more antigens).

The ex vivo sensitizing step can be performed by any method known in the art to stimulate T cells to be antigen-specific ex vivo, such as a method as described in Koehne et al., 2000, Blood 96:109-117; Trivedi et al., 2005, Blood 105:2793-2801; Haque et al., 2007, Blood 110:1123-1131; Hasan et al., 2009, J Immunol 183: 2837-2850; Feuchtinger et al., 2010, Blood 116:4360-4367; Doubrovina et al., 2012, Blood 120:1633-1646; Leen et al., 2013, Blood 121:5113-5123; Papadopoulou et al., 2014, Sci Transl Med 6:242ra83; Sukdolak et al., 2013, Biol Blood Marrow Transplant 19:1480-1492; Koehne et al., 2015, Biol Blood Marrow Transplant 21: 1663-1678; International Patent Application Publication No. WO 2016/073550; International Patent Application Publication No. WO 2016/183153; International Patent Application Publication No. WO 2016/209816; or International Patent Application Publication No. WO 2017/044678.

In specific embodiments, the aforementioned period of time in culture (termed herein "the Sensitization Culture Time;" i.e., the culture time period over which co-culturing occurs) is at least 7 days. In specific embodiments, the Sensitization Culture Time is at least 14 days. In specific embodiments, the Sensitization Culture Time is at least 21 days. In specific embodiments, the Sensitization Culture Time is at least 28 days. In specific embodiments, the Sensitization Culture Time is in the range of 21-28 days. In specific embodiments, the Sensitization Culture Time is in the range of 28-35 days. In a specific embodiment, the Sensitization Culture Time is 21 days. In another specific embodiment, the Sensitization Culture Time is 22 days. In another specific embodiment, the Sensitization Culture Time is 23 days. In another specific embodiment, the Sensitization Culture Time is 24 days. In another specific embodiment, the Sensitization Culture Time is 25 days. In another specific embodiment, the Sensitization Culture Time is 26 days. In another specific embodiment, the Sensitization Culture Time is 27 days. In a preferred embodiment, the Sensitization Culture Time is 28 days. In another specific embodiment, the Sensitization Culture Time is 29 days. In another specific embodiment, the Sensitization Culture Time is 30 days. In another specific embodiment, the Sensitization Culture Time is 31 days. In another specific embodiment, the Sensitization Culture Time is 32 days. In another specific embodiment, the Sensitization Culture Time is 33 days. In another specific embodiment, the Sensitization Culture Time is 34 days. In another specific embodiment, the Sensitization Culture Time is 34 days.

The antigen presenting cells used in the ex vivo sensitizing step can be any antigen presenting cells suitable for presenting the one or more antigens, including professional antigen presenting cells and non-professional antigen presenting cells, and are typically irradiated cells to prevent multiplication of these cells after being added to the culture. In specific embodiments, the antigen presenting cells used in the ex vivo sensitizing step are dendritic cells, cytokine-activated monocytes, peripheral blood mononuclear cells (PBMCs), Epstein-Barr virus-transformed B-lymphoblastoid cell line cells (EBV-BLCL cells), or artificial antigen presenting cells (AAPCs). In a specific embodiment, the antigen presenting cells are dendritic cells. In another specific embodiment, the antigen presenting cells are PBMCs. In another specific embodiment, the antigen presenting cells are EBV-BLCL cells. In another specific embodiment, the antigen presenting cells are AAPCs. In some embodiments, the antigen presenting cells are derived from the donor of the population of human blood cells. In other embodiments, the antigen presenting cells are allogeneic to the donor of the population of human blood cells. The antigen presenting cells can be obtained by any method known in the art, such as the method(s) described in Section 6; Koehne et al., 2000, Blood 96:109-117; Koehne et al., 2002, Blood 99:1730-1740; Trivedi et al., 2005, Blood 105:2793-2801; O'Reilly et al., 2007, Immunol Res 38:237-250; Hasan et al., 2009, J Immunol 183: 2837-2850; Barker et al., 2010, Blood 116: 5045-5049; O'Reilly et al., 2011, Best Practice & Research Clinical Haematology 24:381-391; Doubrovina et al., 2012, Blood 120:1633-1646; Koehne et al., 2015, Biol Blood Marrow Transplant 21: 1663-1678; International Patent Application Publication No. WO 2016/073550; International Patent Application Publication No. WO 2016/183153; International Patent Application Publication No. WO 2016/209816; or International Patent Application Publication No. WO 2017/044678.

In various embodiments, the ex vivo sensitizing further comprises adding antigen presenting cells presenting the one or more antigens to the culture. In specific embodiments, the ex vivo sensitizing further comprises adding antigen presenting cells presenting the one or more antigens to the culture at the initiation of said co-culturing and every 1 to 14 days thereafter during the co-culturing. In specific embodiments, the ex vivo sensitizing further comprises adding antigen presenting cells presenting the one or more antigens to the culture at the initiation of said co-culturing and every 3 to 12 days thereafter during the co-culturing. In specific embodiments, the ex vivo sensitizing further comprises adding antigen presenting cells presenting the one or more antigens to the culture at the initiation of said co-culturing and every 5 to 10 days thereafter during the co-culturing. In preferred embodiments, the ex vivo sensitizing further comprises adding antigen presenting cells presenting the one or more antigens to the culture at the initiation of said co-culturing and every 7 to 10 days thereafter during the co-culturing. In a specific embodiment, the ex vivo sensitizing further comprises adding antigen presenting cells presenting the one or more antigens to the culture at the initiation of said co-culturing and about every 5 days thereafter during the co-culturing. In another specific embodiment, the ex vivo sensitizing further comprises adding antigen presenting cells presenting the one or more antigens to the culture at the initiation of said co-culturing and about every 6 days thereafter during the co-culturing. In another specific embodiment, the ex vivo sensitizing further comprises adding antigen presenting cells presenting the one or more antigens to the culture at the initiation of said co-culturing and about every 7 days thereafter during the co-culturing. In another specific embodiment, the ex vivo sensitizing further comprises adding antigen presenting cells presenting the one or more antigens to the culture at the initiation of said co-culturing and about every 8 days thereafter during the co-culturing. In another specific embodiment, the ex vivo sensitizing further comprises adding antigen presenting cells presenting the one or more antigens to the culture at the initiation of said co-culturing and about every 9 days thereafter during the co-culturing. In another specific embodiment, the ex vivo sensitizing further comprises adding antigen presenting cells presenting the one or more antigens to the culture at the initiation of said co-culturing and about every 10 days thereafter during the co-culturing.

In some embodiments, the antigen presenting cells are loaded with one or more immunogenic peptides or proteins derived from the one or more antigens. Non-limiting exemplary methods for loading antigen presenting cells with peptide(s) derived from antigen(s) can be found in Trivedi et al., 2005, Blood 105:2793-2801; Barker et al., 2010, Blood 116:5045-5049; Doubrovina et al., 2012, Blood 120:1633-1646; Hasan et al., 2009, J Immunol 183: 2837-2850; Koehne et al., 2015, Biol Blood Marrow Transplant 21: 1663-1678; International Patent Application Publication No. WO 2016/073550; International Patent Application Publication No. WO 2016/183153; International Patent Application Publication No. WO 2016/209816; and International Patent Application Publication No. WO 2017/044678. In other embodiments, the antigen presenting cells are genetically engineered to recombinantly express one or more immunogenic peptides or proteins derived from the one or more antigens. Any appropriate method known in the art for introducing nucleic acid vehicles into cells to express proteins, such as transduction or transformation, can be used to genetically engineer the antigen presenting calls to recombinantly express the one or more immunogenic peptides or proteins derived from the one or more antigens.

In some embodiments, the one or more immunogenic peptides or proteins are a pool of overlapping peptides derived from the one or more antigens. In specific embodiments, the pool of overlapping peptides is a pool of overlapping pentadecapeptides. In other embodiments, the one or more immunogenic peptides or proteins are one or more proteins derived from the one or more antigens.

In specific embodiments, the method of generating a population of human cells comprising antigen-specific T cells further comprises, after the step of ex vivo sensitizing, a step of cryopreserving the ex vivo sensitized (and preferably expanded) human T cells, or a fraction thereof. In a specific embodiment, the method of generating a population of human cells comprising antigen-specific T cells further comprises, after the step of cryopreserving, steps of thawing and optionally expanding in culture the ex vivo sensitized (and preferably expanded) and cryopreserved human T cells or a faction thereof. The cryopreserving and thawing steps can be performed by known methods in the art for cryopreserving T cells and thawing T cells, respectively.

The term "about" shall be construed so as to allow normal variation, such as, for example, a variation within 20%.

5.2.2. Genetically Engineered Antigen-Specific T Cells

In other embodiments, the antigen-specific T cells contained in the population of human cells comprising antigen-specific T cells are made antigen-specific by genetically engineering a population of T cells from a population of human blood cells (e.g., by expression of a chimeric antigen receptor (CAR) or T cell receptor (TCR) specific to the one or more antigens of the solid malignant tumor).

In specific embodiments, the antigen-specific T cells recombinantly express one or more chimeric antigen receptors (CARs) recognizing the one or more antigens, and are produced by transducing a population of T cells with one or more nucleic acids encoding the one or more CARs recognizing the one or more antigens.

CARs are engineered receptors that provide both antigen binding and immune cell activation functions (Sadelain et al., 2013, Cancer Discovery 3:388-398). They usually comprise an antigen-binding domain (e.g., derived from a monoclonal antibody or the extracellular domain of a receptor), a transmembrane domain, an intracellular domain, and optionally a co-stimulatory domain. CARs can be used to graft the specificity of an antigen-binding domain onto an immune cell such as a T cell.

The population of T cells transduced with one or more nucleic acids encoding the one or more CARs can be generated by any method known in the art, for example, as described in Stauss et al., 2015, Curr Opin Pharmacol 24:113-118; Sharpe and Mount, 2015, Dis Model Mech 8:337-350; or Park et al., 2011, Trends Biotechnol 29:550-557.

The nucleic acid encoding a CAR can be DNA, RNA, or a nucleic acid analog. In specific embodiments, such a nucleic acid may be part of a vector. In a specific embodiment, the vector is an expression vector that is capable of directing the expression of a nucleic acid encoding a polypeptide of the CAR described herein in T cells. Non-limiting examples of expression vectors suitable for directing the expression of a nucleic acid encoding a polypeptide of the CAR described herein include, but are not limited to, plasmids and viral vectors, such as synthetic vectors, lentiviral vectors, replication-defective retroviral vectors, or autonomously replicating plasmids. In a specific embodiment, an expression vector used for directing the expression of a nucleic acid encoding a polypeptide of the CAR described herein includes one or more regulatory sequences operably linked to the nucleic acid to be expressed. "Operably linked" is intended to mean that a nucleic acid of interest is linked to the regulatory sequence(s) in a manner which allows for expression of the nucleic acid in T cells. Regulatory sequences include promoters, enhancers and other expression control elements (e.g., polyadenylation signals).

A nucleic acid encoding a polypeptide of the CAR described herein, for example, an expression vector, can be transduced into host cells via conventional transformation or transfection (such as, transfection by a virus, e.g., a retrovirus or lentivirus) techniques. Such techniques include, but are not limited to, calcium phosphate or calcium chloride co-precipitation, DEAE-dextran-mediated transfection, lipofection, and electroporation. Cells containing a nucleic acid encoding a polynucleotide of the CAR described herein may be selected using one or more selectable markers known in the art.

In specific embodiments, the antigen-specific T cells recombinantly express one or more T cell receptors (TCRs) recognizing the one or more antigens, and are produced by transducing a population of T cells with one or more nucleic acids encoding the one or more TCRs recognizing the one or more antigens; thereby producing the human antigen-specific T cells.

TCR is a cell surface molecule on T cells that is responsible for recognizing antigen peptide-bound major histocompatibility complex (MHC) molecules.

The population of T cells transduced with one or more nucleic acids encoding the one or more TCRs can be generated by any method known in the art, for example, as described in Stauss et al., 2015, Curr Opin Pharmacol 24:113-118; Sharpe and Mount, 2015, Dis Model Mech 8:337-350; Kunert et al., 2013, Front Immunol 4: 363; Stone et al., 2012, Methods Enzymol 503:189-222; or Park et al., 2011, Trends Biotechnol 29:550-557.

The nucleic acid encoding a TCR can be DNA, RNA, or a nucleic acid analog. In specific embodiments, such a nucleic acid may be part of a vector. In a specific embodiment, the vector is an expression vector that is capable of directing the expression of a nucleic acid encoding a polypeptide of the TCR described herein in T cells. Non-limiting examples of expression vectors suitable for directing the expression of a nucleic acid encoding a polypeptide of the TCR described herein include, but are not limited to, plasmids and viral vectors, such as synthetic vectors, lentiviral vectors, replication-defective retroviral vectors, or autonomously replicating plasmids. In a specific embodiment, an expression vector used for directing the expression of a nucleic acid encoding a polypeptide of the TCR described herein includes one or more regulatory sequences operably linked to the nucleic acid to be expressed. "Operably linked" is intended to mean that a nucleic acid of interest is linked to the regulatory sequence(s) in a manner which allows for expression of the nucleic acid in T cells. Regulatory sequences include promoters, enhancers and other expression control elements (e.g., polyadenylation signals).

A nucleic acid encoding a polypeptide of the TCR described herein, for example, an expression vector, can be transduced into host cells via conventional transformation or transfection (such as, transfection by a virus, e.g., a retrovirus or lentivirus) techniques. Such techniques include, but are not limited to, calcium phosphate or calcium chloride co-precipitation, DEAE-dextran-mediated transfection, lipofection, and electroporation. Cells containing a nucleic acid encoding a polynucleotide of the TCR described herein may be selected using one or more selectable markers known in the art.

In a specific embodiment, the antigen-specific T cells contained in the population of human cells comprising antigen-specific T cells have been expanded in culture. In another specific embodiment, the antigen-specific T cells contained in the population of human cells comprising antigen-specific T cells are thawed from a cryopreserved form. In another specific embodiment, the antigen-specific T cells contained in the population of human cells comprising antigen-specific T cells are thawed and expanded from a cryopreserved form. The cryopreservation and thawing can be performed by known methods in the art for cryopreserving T cells and thawing T cells, respectively.

5.2.3. Antigen-Specific T Cells Purified from a Blood-Derived Sample

In other embodiments, the antigen-specific T cells contained in the population of human cells comprising antigen-specific T cells are or are expanded from antigen-specific T cells purified from a population of human blood cells (such as peripheral blood mononuclear cells (PBMCs)) derived from a human blood sample that is seropositive for the one or more antigens (for example, by sorting (such as fluorescence activated cell sorting) T cells that recognize the one or more antigens from the blood sample cells).

In a specific embodiment, the antigen-specific T cells contained in the population of human cells comprising antigen-specific T cells have been expanded in culture. In another specific embodiment, the antigen-specific T cells contained in the population of human cells comprising antigen-specific T cells are thawed from a cryopreserved form. In another specific embodiment, the antigen-specific T cells contained in the population of human cells comprising antigen-specific T cells are thawed and expanded from a cryopreserved form. The cryopreservation and thawing can be performed by known methods in the art for cryopreserving T cells and thawing T cells, respectively.

5.2.4. The Population of Human Blood Cells

The human blood cell sample described in Sections 5.2.1-5.2.3 can be any cell sample that contains T cells, such as, but is not limited to, a hematopoietic cell sample, a fractionated or unfractionated whole blood sample, a fractionated or unfractionated apheresis collection (e.g., a leukapheresis collection, such as leukopak), PBMCs, or a purified T cell population (e.g., T cells enriched from PBMCs). In a specific embodiment, the human blood cell sample is a human PBMC sample. PBMCs can be isolated from the blood sample by any method known in the art to isolate PBMCs from a blood sample, such as by Ficoll-Hypaque centrifugation as described in Koehne et al., 2000, Blood 96:109-117 or Trivedi et al., 2005, Blood 105:2793-2801. In another specific embodiment, the human blood cell sample is a population enriched in T cells from PBMCs. T cells can be enriched for from the PBMCs by any method known in the art to enrich for T cells from a blood sample or PBMCs. Non-limiting exemplary methods for enriching for T cells from PBMCs can be found in Koehne et al., 2000, Blood 96:109-117; Trivedi et al., 2005, Blood 105:2793-2801; Hasan et al., 2009, J Immunol 183: 2837-2850; and Koehne et al., 2015, Biol Blood Marrow Transplant 21: 1663-1678. For example, T cells can be enriched for from PBMCs by sorting the PBMCs using an anti-CD3 antibody and/or depleting from the PBMCs adherent monocytes and natural killer cells.

In preferred embodiments, the population of human blood cells is derived from a human donor that is seropositive for the one or more antigens. In certain embodiments, the population of human blood cells is derived from a human donor that is seronegative for the one or more antigens.

In some embodiments, the population of human blood cells is derived autologously from the human patient. In other embodiments, the population of human blood cells is derived from a human donor that is allogeneic to the human patient. In a specific embodiment, the human patient has been the recipient of a transplant from a transplant donor, and the human donor from whom the population of human blood cells is derived is a third-party donor that is different from the transplant donor. In another specific embodiment, the human patient has been the recipient of a transplant from a transplant donor, and the human donor from whom the population of human blood cells is derived is the transplant donor. The transplant can be a hematopoietic stem cell transplant (HSCT) (such as a peripheral blood stem cell transplant, a bone marrow transplant, or a cord blood transplant) or a solid organ transplant (such as a kidney transplant, a liver transplant, a heart transplant, an intestinal transplant, a pancreas transplant, a lung transplant, or a small bowel transplant).

The human donor from whom the population of human blood cells is derived can be an adult (at least age 16), an adolescent (age 12-15), a child (under age 12), a fetus, or a neonate. In a specific embodiment, the human donor from whom the population of human blood cells is derived is an adult. In a specific embodiment, the population of human blood cells is derived from human (umbilical) cord blood.

In specific embodiments, the population of human blood cells used for generating a population of human cells comprising antigen-specific T cells described herein comprises $CD4^+$ T cells. In specific embodiments, the population of human blood cells used for generating a population of human cells comprising antigen-specific T cells described herein comprises $CD8^+$ T cells. In a preferred embodiment, the population of human blood cells used for generating a population of human cells comprising antigen-specific T cells described herein comprises both $CD4^+$ and $CD8^+$ T cells.

In a specific embodiment, the population of human blood cells used for generating a population of human cells comprising antigen-specific T cells described herein contains at least 50% T cells. In another specific embodiment, the population of human blood cells contains at least 60% T cells. In another specific embodiment, the population of human blood cells contains at least 70% T cells. In a specific embodiment, the population of human blood cells contains at least 80% T cells. In a specific embodiment, the population of human blood cells contains at least 90% T cells. In a specific embodiment, the population of human blood cells contains at least 95% T cells. In a specific embodiment, the population of human blood cells contains at least 99% T cells. In a specific embodiment, the population of human blood cells contains 100% T cells.

In certain embodiments, the population of human blood cells used for generating a population of human cells comprising antigen-specific T cells described herein contains, at initiation of generation, at least 50% memory T cells. In a specific embodiment, the population of human blood cells used for generating a population of human cells comprising antigen-specific T cells described herein contains, at initiation of generation, at least 60% memory T cells. In another specific embodiment, the population of human blood cells used for generating a population of human cells comprising antigen-specific T cells described herein contains, at initiation of generation, at least 70% memory T cells. In another specific embodiment, the population of human blood cells used for generating a population of human cells comprising antigen-specific T cells described herein contains, at initiation of generation, at least 80% memory T cells. In another specific embodiment, the population of human blood cells used for generating a population of human cells comprising antigen-specific T cells described herein contains, at initiation of generation, at least 90% memory T cells. In another specific embodiment, the population of human blood cells used for generating a population of human cells comprising antigen-specific T cells described herein contains, at initiation of generation, at least 95% memory T cells. In another specific embodiment, the population of human blood cells used for generating a population of human cells comprising antigen-specific T cells described herein contains, at initiation of generation, at least 99% memory T cells. In another specific embodiment, the population of human blood cells used for generating a population of human cells comprising antigen-specific T cells described herein contains, at initiation of generation, 100% memory T cells. The memory T cells described herein can be central memory T cells ($T_{CM}$ cells), stem cell-like memory T cells ($T_{SCM}$ cells), effector memory T cells ($T_{EM}$ cells), or a combination thereof.

5.3. Characteristics of the Population of Human Cells Comprising Antigen-Specific T Cells To be suitable for therapeutic administration to a human patient in adoptive immunotherapy for a solid malignant tumor, the population of human cells comprising antigen-specific T cells described herein preferably (1) exhibits substantial antigen reactivity (for example, cytotoxicity) toward fully or partially HLA-matched (relative to the population of human cells) target antigen presenting cells that present the one or more antigens of the solid malignant tumor (e.g., target antigen presenting cells that are loaded with or genetically engineered to express one or more peptides or proteins derived from the one or more antigens of the solid malignant tumor); (2) lacks substantial alloreactivity; and (3) is restricted (i.e., the antigen-specific T cells contained in the population of human cells comprising antigen-specific T cells are restricted) by an HLA allele shared with the tumor cells in the human patient, and/or shares (i.e., the antigen-specific T cells contained in the population of human cells comprising antigen-specific T cells share) at least 2 HLA alleles (e.g., at least 2 out of 10 HLA alleles) with the tumor cells in the human patient. Thus, preferably, antigen reactivity (for example, cytotoxicity), alloreactivity, information as to which HLA allele(s) the population of human cells comprising antigen-specific T cells is restricted (i.e., to which HLA allele(s) the antigen-specific T cells contained in the population of human cells comprising antigen-specific T cells are restricted), and/or the HLA assignment of the population of human cells comprising antigen-specific T cells (i.e., the HLA assignment of the antigen-specific T cells contained in the population of human cells comprising antigen-specific T cells) are measured by a method known in the art before administration to a human patient (for example, such a method as described in Koehne et al., 2002, Blood 99:1730-1740; Koehne et al., 2000, Blood 96:109-117; Trivedi et al., 2005, Blood 105: 2793-2801; Haque et al., 2007, Blood 110:1123-1131; Hasan et al., 2009, J Immunol 183: 2837-2850; Feuchtinger et al., 2010, Blood 116:4360-4367; Doubrovina et al., 2012, Blood 120:1633-1646; Leen et al., 2013, Blood 121:5113-5123; Papadopoulou et al., 2014, Sci Transl Med 6:242ra83; Sukdolak et al., 2013, Biol Blood Marrow Transplant 19:1480-1492; Koehne et al., 2015, Biol Blood Marrow Transplant 21: 1663-1678; Weren et al., J Immunol Methods, 289:17-26; Shafer-Weaver et al., 2003, J Transl Med 1:14; Nagorsen and Marincola, ed., 2005, Analyzing T Cell Responses: How to Analyze Cellular Immune Responses against Tumor Associated Antigens, Springer Netherlands; International Patent Application Publication No. WO 2016/073550; International Patent Application Publication No. WO 2016/183153; International Patent Application Publication No. WO 2016/209816; or International Patent Application Publication No. WO 2017/044678). In addition, the population of human cells comprising antigen-specific T cells shall be microbial sterile to be suitable for therapeutic administration. Microbial sterility can be verified by any method known in the art for assaying microbial sterility, for example, by demonstrating negative cultures for bacteria, fungi and mycoplasma and endotoxin levels 5 EU/ml cell dose.

A cell bank comprising a plurality of isolated populations of human cells comprising antigen-specific T cells described herein can also be generated. Preferably, information as to antigen reactivity (for example, cytotoxicity), alloreactivity, HLA restriction, and/or assignment is ascertained for each of the plurality of isolated populations of human cells comprising antigen-specific T cells contained in the cell bank, and linked to the identifier of the corresponding population of human cells comprising antigen-specific T cells, so as to facilitate the selection of a suitable population of human cells comprising antigen-specific T cells from the plurality for therapeutic administration to a human patient.

Preferably, the population of human cells comprising antigen-specific T cells is enriched for T cells. In a specific embodiment, the population of human cells comprising antigen-specific T cells contains at least 70% T cells. In another specific embodiment, the population of human cells comprising antigen-specific T cells contains at least 80% T cells. In another specific embodiment, the population of human cells comprising antigen-specific T cells contains at least 90% T cells. In another specific embodiment, the population of human cells comprising antigen-specific T cells contains at least 95% T cells. In another specific embodiment, the population of human cells comprising antigen-specific T cells contains at least 99% T cells. In another specific embodiment, the population of human cells comprising antigen-specific T cells contains 100% T cells. In a specific embodiment, the population of human cells comprising antigen-specific T cells contains at least 70% $CD3^+$ cells. In another specific embodiment, the population of human cells comprising antigen-specific T cells contains at least 80% $CD3^+$ cells. In another specific embodiment, the population of human cells comprising antigen-specific T cells contains at least 90% $CD3^+$ cells. In another specific embodiment, the population of human cells comprising antigen-specific T cells contains at least 95% $CD3^+$ cells. In another specific embodiment, the population of human cells comprising antigen-specific T cells contains at least 99% $CD3^+$ cells. In another specific embodiment, the population of human cells comprising antigen-specific T cells contains 100% $CD3^+$ cells.

In a specific embodiment, the population of human cells comprising antigen-specific T cells contains less than 5% natural killer (NK) cells. In another specific embodiment, the population of human cells comprising antigen-specific T cells contains less than 2% NK cells. In another specific embodiment, the population of human cells comprising antigen-specific T cells contains less than 1% NK cells. In another specific embodiment, the population of human cells comprising antigen-specific T cells contains no NK cells.

In a specific embodiment, the population of human cells comprising antigen-specific T cells contains less than 5% B cells. In another specific embodiment, the population of human cells comprising antigen-specific T cells contains less than 2% B cells. In another specific embodiment, the population of human cells comprising antigen-specific T cells contains less than 1% B cells. In another specific embodiment, the population of human cells comprising antigen-specific T cells contains no B cells.

In a specific embodiment, the population of human cells comprising antigen-specific T cells comprises $CD4^+$ T cells. In another specific embodiment, the population of human cells comprising antigen-specific T cells comprises $CD8^+$ T cells. In a preferred embodiment, the population of human cells comprising antigen-specific T cells comprises both $CD8^+$ and $CD4^+$ T cells.

5.3.1. Cytotoxicity and Other Measures of Antigen Reactivity

The antigen reactivity (for example, cytotoxicity) of a population of human cells comprising antigen-specific T cells described herein toward fully or partially HLA-matched (relative to the population of human cells) target antigen presenting cells can be determined by any assay known in the art to measure T cell mediated antigen reactivity (for example, cytotoxicity), such as, but is not limited to, a method described in Nagorsen and Marincola, ed., 2005, Analyzing T Cell Responses: How to Analyze Cellular Immune Responses against Tumor Associated Antigens, Springer Netherlands. The assay can be performed using the population of human cells comprising antigen-specific T cells directly, an aliquot thereof, or a precursor cell population that indicates the antigen reactivity (for example, cytotoxicity) of the population of human cells comprising antigen-specific T cells. In a specific embodiment, the antigen reactivity (for example, cytotoxicity) is determined by a standard $^{51}Cr$ release assay, an IFN-γ-production assay, a limiting dilution assay to measure CTL precursors (CTLps), a perforin release assay, a granzyme B release assay, or a CD107 mobilization assay, as described in Trivedi et al., 2005, Blood 105:2793-2801; Hasan et al., 2009, J Immunol 183: 2837-2850; Doubrovina et al., 2012, Blood 119:2644-2656; Koehne et al., 2002, Blood 99:1730-1740; Koehne et al., 2000, Blood 96:109-117; Weren et al., J Immunol Methods, 289:17-26; Shafer-Weaver et al., 2003, J Transl Med 1:14; or Nagorsen and Marincola, ed., 2005, Analyzing T Cell Responses: How to Analyze Cellular Immune Responses against Tumor Associated Antigens, Springer Netherlands.

In certain embodiments, the population of human cells comprising antigen-specific T cells described herein exhibits substantial antigen reactivity (for example, cytotoxicity) in vitro toward (e.g., exhibits substantial lysis of) fully or partially HLA-matched (preferably, fully or partially HLA-matched at high resolution) target antigen presenting cells that present the one or more antigens of the solid malignant tumor (e.g., target antigen presenting cells that are loaded with or genetically engineered to express one or more peptides or proteins derived from the one or more antigens of the solid malignant tumor). Preferably, the fully or partially HLA-matched target antigen presenting cells are fully HLA-matched target antigen presenting cells (e.g., target antigen presenting cells derived from the human donor of the population of human blood cells used to generate the population of human cells). In specific embodiments, the population of human cells comprising antigen-specific T cells described herein exhibits lysis of greater than or equal to 20%, 25%, 30%, 35%, or 40% of the fully or partially HLA-matched target antigen presenting cells that present the one or more antigens of the solid malignant tumor (e.g., target antigen presenting cells that are loaded with or genetically engineered to express one or more peptides or proteins derived from the one or more antigens of the solid malignant tumor). In a specific embodiment, the population of human cells comprising antigen-specific T cells described herein exhibits lysis of greater than or equal to 20% of the fully or partially HLA-matched target antigen presenting cells that present the one or more antigens of the solid malignant tumor (e.g., target antigen presenting cells that are loaded with or genetically engineered to express one or more peptides or proteins derived from the one or more antigens of the solid malignant tumor). In another specific embodiment, the population of human cells comprising antigen-specific T cells described herein exhibits lysis of greater than or equal to 25% of the fully or partially HLA-matched target antigen presenting cells that present the one or more antigens of the solid malignant tumor (e.g., target antigen presenting cells that are loaded with or genetically engineered to express one or more peptides or proteins derived from the one or more antigens of the solid malignant tumor).

In a specific embodiment, the antigen reactivity (for example, cytotoxicity) exhibited by the population of human cells comprising antigen-specific T cells described herein is at least 2-fold higher than the antigen reactivity (for example, cytotoxicity) normally exhibited by unselected donor lymphocytes from human blood, e.g., as used in donor lymphocyte infusions. In another specific embodiment, the antigen reactivity (for example, cytotoxicity) exhibited by the population of human cells comprising antigen-specific T cells described herein is at least 5-fold higher than the antigen reactivity (for example, cytotoxicity) normally exhibited by unselected donor lymphocytes used in donor lymphocyte infusions. In another specific embodiment, the antigen reactivity (for example, cytotoxicity) exhibited by the population of human cells comprising antigen-specific T cells described herein is at least 10-fold higher than the antigen reactivity (for example, cytotoxicity) normally exhibited by unselected donor lymphocytes used in donor lymphocyte infusions. In another specific embodiment, the antigen reactivity (for example, cytotoxicity) exhibited by the population of human cells comprising antigen-specific T cells described herein is at least 20-fold higher than the antigen reactivity (for example, cytotoxicity) normally exhibited by unselected donor lymphocytes used in donor lymphocyte infusions. In another specific embodiment, the antigen reactivity (for example, cytotoxicity) exhibited by the population of human cells comprising antigen-specific T cells described herein is at least 50-fold higher than the antigen reactivity (for example, cytotoxicity) normally exhibited by unselected donor lymphocytes used in donor lymphocyte infusions. In another specific embodiment, the antigen reactivity (for example, cytotoxicity) exhibited by the population of human cells comprising antigen-specific T cells described herein is at least 100-fold higher than the antigen reactivity (for example, cytotoxicity) normally exhibited by unselected donor lymphocytes used in donor lymphocyte infusions. In another specific embodiment, the antigen reactivity (for example, cytotoxicity) exhibited by the population of human cells comprising antigen-specific T cells described herein is at least 200-fold higher than the antigen reactivity (for example, cytotoxicity) normally exhibited by unselected donor lymphocytes used in donor lymphocyte infusions. In another specific embodiment, the antigen reactivity (for example, cytotoxicity) exhibited by the population of human cells comprising antigen-specific T cells described herein is at least 500-fold higher than the antigen reactivity (for example, cytotoxicity) normally exhibited by unselected donor lymphocytes used in donor lymphocyte infusions. In another specific embodiment, the antigen reactivity (for example, cytotoxicity) exhibited by the population of human cells comprising antigen-specific T cells described herein is at least 1000-fold higher than the antigen reactivity (for example, cytotoxicity) normally exhibited by unselected donor lymphocytes used in donor lymphocyte infusions.

Target antigen presenting cells that can be used in the antigen reactivity (for example, cytotoxicity) assay include, but are not limited to, dendritic cells, phytohaemagglutinin (PHA)-lymphoblasts, macrophages, B-cells that generate antibodies, EBV-BLCL cells, and artificial antigen presenting cells (AAPCs). Target antigen presenting cells that can be used in the antigen reactivity (for example, cytotoxicity) assay can be either professional antigen presenting cells or non-professional antigen presenting cells.

In a specific embodiment, multiple iterations of an antigen reactivity (for example, cytotoxicity) assay are performed, wherein different populations of target antigen presenting cells are used that present the same target antigen(s) of the solid malignant tumor in the multiple iterations of the assay, and the antigen reactivity of the population of human cells comprising antigen-specific T cells preferably is the average value of the different iterations of the assay. The multiple iterations of an antigen reactivity (for example, cytotoxicity) assay preferably are performed under essentially the same conditions. The different populations of target antigen presenting cells can be of different types (for example, one population of target antigen presenting cells can be PHA-lymphoblasts, while another population of target antigen presenting cells can be EBV-BLCL cells), but preferably are of the same type (for example, all of the different populations of target antigen presenting cells are PHA-lymphoblasts).

In specific embodiments, the fully or partially HLA-matched target antigen presenting cells used in the antigen reactivity (for example, cytotoxicity) assay are loaded with a pool of peptides derived from the one or more antigens of the solid malignant tumor. The pool of peptides, can be, for example, a pool of overlapping peptides (e.g., pentadecapeptides) spanning the sequence(s) of the one or more antigens of the solid malignant tumor.

5.3.2. Alloreactivity

Alloreactivity of a population of human cells comprising antigen-specific T cells described herein can be measured using an antigen reactivity (for example, cytotoxicity) assay known in the art to measure T cell mediated antigen reactivity (for example, cytotoxicity), such as, but is limited to, a standard $^{51}$Cr release assay, an IFN-γ-production assay, a limiting dilution assay to measure CTL precursors (CTLps), a perforin release assay, a granzyme B release assay, a CD107 mobilization assay, or any other antigen reactivity assay as described in Section 5.3.1, but with target antigen presenting cells that do not present the one or more antigens of the solid malignant tumor (e.g., target antigen presenting cells that are not loaded with or genetically engineered to express one or more peptides or proteins derived from the one or more antigens of the solid malignant tumor), and/or completely HLA-mismatched (preferably, completely HLA-mismatched at low resolution and/or completely HLA supertype mismatched, wherein the HLA supertypes are classified on the basis of their main anchor specificity (see, for example, as described in Sidney et al., 2008, BMC Immunology 9:1)) (relative to the population of human cells) target antigen presenting cells. The assay can be performed using the population of human cells comprising antigen-specific T cells directly, an aliquot thereof, or a precursor cell population that indicates the alloreactivity of the population of human cells comprising antigen-specific T cells. A population of human cells comprising antigen-specific T cells that lacks substantial alloreactivity results generally in the absence of graft-versus-host disease (GvHD) when administered to a human patient.

In certain embodiments, the population of human cells comprising antigen-specific T cells described herein lacks substantial antigen reactivity (for example, cytotoxicity) in vitro toward target antigen presenting cells that do not present the one or more antigens of the solid malignant tumor (e.g., target antigen presenting cells that are not loaded with or genetically engineered to express one or more peptides or proteins derived from the one or more antigens of the solid malignant tumor). In a specific embodiment, such target antigen presenting cells are completely HLA-mismatched (preferably, completely HLA-mismatched at low resolution and/or completely HLA supertype mismatched, wherein the HLA supertypes are classified on the basis of their main anchor specificity (see, for example, as described in Sidney et al., 2008, BMC Immunology 9:1)) relative to the population of human cells. In another specific embodiment, such target antigen presenting cells are fully or partially HLA-matched relative to the population of human cells (e.g., target antigen presenting cells are derived from the human donor of the population of human blood cells used to generate the population of human cells). In specific embodiments, the population of human cells comprising antigen-specific T cells described herein lyses less than or equal to 15%, 10%, 5%, 2%, or 1% of target antigen presenting cells that do not present the one or more antigens of the solid malignant tumor (e.g., target antigen presenting cells that are not loaded with or genetically engineered to express one or more peptides or proteins derived from the one or more antigens of the solid malignant tumor). In a specific embodiment, the population of human cells comprising antigen-specific T cells described herein lyses less than or equal to 10% of target antigen presenting cells that do not present the one or more antigens of the solid malignant tumor (e.g., target antigen presenting cells that are not loaded with or genetically engineered to express one or more peptides or proteins derived from the one or more antigens of the solid malignant tumor). In another specific embodiment, the population of human cells comprising antigen-specific T cells described herein lyses less than or equal to 10% of target antigen presenting cells that do not present the one or more antigens of the solid malignant tumor (e.g., target antigen presenting cells that are not loaded with or genetically engineered to express one or more peptides or proteins derived from the one or more antigens of the solid malignant tumor). In another specific embodiment, the population of human cells comprising antigen-specific T cells described herein lyses less than or equal to 5% of target antigen presenting cells that do not present the one or more antigens of the solid malignant tumor (e.g., target antigen presenting cells that are not loaded with or genetically engineered to express one or more peptides or proteins derived from the one or more antigens of the solid malignant tumor).

In certain embodiments, the population of human cells comprising antigen-specific T cells described herein lacks substantial antigen reactivity (for example, cytotoxicity) in vitro toward completely HLA-mismatched (preferably, completely HLA-mismatched at low resolution and/or completely HLA supertype mismatched, wherein the HLA supertypes are classified on the basis of their main anchor specificity (see, for example, as described in Sidney et al., 2008, BMC Immunology 9:1)) (relative to the population of human cells) target antigen presenting cells. In a specific embodiment, such target antigen presenting cells present the one or more antigens of the solid malignant tumor (e.g., are loaded with or genetically engineered to express one or more peptides or proteins derived from the one or more antigens of the solid malignant tumor). In a preferred embodiment, such target antigen presenting cells do not present the one or more antigens of the solid malignant tumor (e.g., are not loaded with or genetically engineered to express one or more peptides or proteins derived from the one or more antigens of the solid malignant tumor). In specific embodiments, the population of human cells comprising antigen-specific T cells described herein lyses less than or equal to 15%, 10%, 5%, 2%, or 1% of completely HLA-mismatched (relative to the population of human cells) target antigen presenting cells. In a specific embodiment, the population of human cells comprising antigen-specific T cells described herein lyses less than or equal to 10% of completely HLA-mismatched (relative to the population of human cells) target antigen presenting cells. In another specific embodiment, the population of human cells comprising antigen-specific T cells described herein lyses less than or equal to 5% of completely HLA-mismatched (relative to the population of human cells) target antigen presenting cells.

In a specific embodiment, the alloreactivity exhibited by the population of human cells comprising antigen-specific T cells described herein is at least 2-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 5-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 10-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 20-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 50-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 100-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 200-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 500-fold lower than the alloreactivity normally exhibited by unselected donor lymphocytes used in donor lymphocyte infusions. In another specific embodiment, the alloreactivity exhibited by the population of human cells comprising antigen-specific T cells described herein is at least 1000-fold lower than the alloreactivity normally exhibited by unselected donor lymphocytes used in donor lymphocyte infusions.

In certain embodiments, the population of human cells comprising antigen-specific T cells described herein lacks substantial antigen reactivity (for example, cytotoxicity) in vitro toward target antigen presenting cells that do not present the one or more antigens of the solid malignant tumor (e.g., target antigen presenting cells that are not loaded with or genetically engineered to express one or more peptides or proteins derived from the one or more antigens of the solid malignant tumor), as described above, and lacks substantial antigen reactivity (for example, cytotoxicity) in vitro toward completely HLA-mismatched (preferably, completely HLA-mismatched at low resolution and/or completely HLA supertype mismatched, wherein the HLA supertypes are classified on the basis of their main anchor specificity (see, for example, as described in Sidney et al., 2008, BMC Immunology 9:1)) target antigen presenting cells as described above.

In a specific embodiment, the population of human cells comprising antigen-specific T cells described herein contains less than 500, less than 300, or less than 100 alloreactive cytotoxic T lymphocyte precursors (CTLps) per million cells, when the amount of alloreactive CTLps per million cells is determined to be the average amount of alloreactive CTLps per million cells determined in N limiting dilution assays, each assay using a different population of target antigen presenting cells that are completely HLA-mismatched (preferably, completely HLA-mismatched at low resolution and/or completely HLA supertype mismatched, wherein the HLA supertypes are classified on the basis of their main anchor specificity (see, for example, as described in Sidney et al., 2008, BMC Immunology 9:1)) relative to the population of human cells, wherein each different population of target antigen presenting cells is of different HLA type, wherein N is an integer greater than 1. In another specific embodiment, the population of human cells comprising antigen-specific T cells described herein contains less than 100 alloreactive cytotoxic T lymphocyte precursors (CTLps) per million cells, when the amount of alloreactive CTLps per million cells is determined to be the average amount of alloreactive CTLps per million cells determined in N limiting dilution assays, each assay using a different population of target antigen presenting cells that are completely HLA-mismatched (preferably, completely HLA-mismatched at low resolution and/or completely HLA supertype mismatched, wherein the HLA supertypes are classified on the basis of their main anchor specificity (see, for example, as described in Sidney et al., 2008, BMC Immunology 9:1)) relative to the population of human cells, wherein each different population of target antigen presenting cells is of different HLA type, wherein N is an integer greater than 1. In another specific embodiment, the population of human cells comprising antigen-specific T cells described herein contains less than 150 alloreactive cytotoxic T lymphocyte precursors (CTLps) per million cells, when the amount of alloreactive CTLps per million cells is determined to be the average amount of alloreactive CTLps per million cells determined in N limiting dilution assays, each assay using a different population of target antigen presenting cells that are completely HLA-mismatched (preferably, completely HLA-mismatched at low resolution and/or completely HLA supertype mismatched, wherein the HLA supertypes are classified on the basis of their main anchor specificity (see, for example, as described in Sidney et al., 2008, BMC Immunology 9:1)) relative to the population of human cells, wherein each different population of target antigen presenting cells is of different HLA type, wherein N is an integer greater than 1. In a specific embodiment, N is greater than 2. In another specific embodiment, N is greater than 3. In another specific embodiment, N is greater than 4. In another specific embodiment, N equals 2. In another specific embodiment, N equals 3. In another specific embodiment, N equals 4. Preferably, N equals 5. While each population of target antigen presenting cells used in the limiting dilution assays may present the one or more antigens of the solid malignant tumor (e.g., are loaded with or genetically engineered to express one or more peptides or proteins derived from the one or more antigens of the solid malignant tumor), in a preferred embodiment, each population of target antigen presenting cells used in the limiting dilution assays does not present the one or more antigens of the solid malignant tumor (e.g., are not loaded with or genetically engineered to express one or more peptides or proteins derived from the one or more antigens of the solid malignant tumor). By way of example, when the target antigen presenting cells do not express and are not loaded with one or more peptides or proteins derived from the one or more antigens of the solid malignant tumor, the target antigen presenting cells cannot and thus do not present such antigens. The limiting dilution assays can be performed by any method known in the art, for example, as described in Doubrovina et al., 2012, Blood 119:2644-2656; Koehne et al., 2002, Blood 99:1730-1740; or Koehne et al., 2000, Blood 96:109-117. Preferably, the limiting dilution assays are performed under essentially the same conditions.

Target antigen presenting cells that can be used in the alloreactivity assay include, but are not limited to, dendritic cells, phytohaemagglutinin (PHA)-lymphoblasts, macrophages, B-cells that generate antibodies, EBV-BLCL cells, and artificial antigen presenting cells (AAPCs). Target antigen presenting cells that can be used in the alloreactivity assay can be either professional antigen presenting cells or non-professional antigen presenting cells.

In a specific embodiment, multiple iterations of an alloreactivity assay are performed, wherein different populations of target antigen presenting cells are used in the multiple iterations of the assay, the alloreactivity of the population of human cells comprising antigen-specific T cells preferably is the average value of the different iterations of the assay. The multiple iterations of an alloreactivity assay preferably are performed under essentially the same conditions. The different populations of target antigen presenting cells can be of different types (for example, one population of target antigen presenting cells can be PHA-lymphoblasts, while another population of target antigen presenting cells can be EBV-BLCL cells), but preferably are of the same type (for example, all of the different populations of target antigen presenting cells are PHA-lymphoblasts).

5.3.3. HLA Type

The HLA assignment (i.e., the HLA loci type) of a population of human cells comprising antigen-specific T cells described herein (i.e., the HLA assignment of the antigen-specific T cells contained in the population of human cells comprising antigen-specific T cells) and/or the HLA assignment of the tumor cells in the human patient to be treated can be ascertained (i.e., typed) by any method known in the art for typing HLA alleles. The assignment can be performed using the population of human cells comprising antigen-specific T cells directly, an aliquot thereof, or a precursor cell population that indicates the HLA assignment of the population of human cells comprising antigen-specific T cells. Non-limiting exemplary methods for ascertaining the HLA assignment can be found in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Hurley, "DNA-based typing of HLA for transplantation." in Leffell et al., eds., 1997, Handbook of Human Immunology, Boca Raton: CRC Press; Dunn, 2011, Int J Immunogenet 38:463-473; Erlich, 2012, Tissue Antigens, 80:1-11; Bontadini, 2012, Methods, 56:471-476; and Lange et al., 2014, BMC Genomics 15: 63. In specific embodiments, at least 4 HLA loci (preferably HLA-A, HLA-B, HLA-C, and HLA-DR) are typed. In a specific embodiment, 4 HLA loci (preferably HLA-A, HLA-B, HLA-C, and HLA-DR (preferably HLA-DRB1)) are typed. In another specific embodiment, 5 HLA loci (preferably HLA-A, HLA-B, HLA-C, HLA-DR (preferably HLA-DRB1), and HLA-DQ (preferably HLA-DQB1)) are typed. In another specific embodiment, 6 HLA loci are typed. In another specific embodiment, 8 HLA loci are typed. In another specific embodiment, 10 HLA loci are typed.

In general, high-resolution typing is preferable for HLA typing. The high-resolution typing can be performed by any method known in the art, for example, as described in ASHI Laboratory Manual, Edition 4.2 (2003), American Society for Histocompatibility and Immunogenetics; ASHI Laboratory Manual, Supplements 1 (2006) and 2 (2007), American Society for Histocompatibility and Immunogenetics; Flomenberg et al., Blood, 104:1923-1930; Kogler et al., 2005, Bone Marrow Transplant, 36:1033-1041; Lee et al., 2007, Blood 110:4576-4583; Erlich, 2012, Tissue Antigens, 80:1-11; Lank et al., 2012, BMC Genomics 13:378; or Gabriel et al., 2014, Tissue Antigens, 83:65-75.

In specific embodiments, the HLA assignment of the tumor cells in the human patient to be treated is ascertained by typing the origin of the tumor cells (e.g., the human patient or a transplant donor for the human patient, as the case may be). The origin of the tumor cells can be determined by any method known in the art, for example, by analyzing variable tandem repeats (VTRs) (which is a method that uses unique DNA signature of small DNA sequences of different people to distinguish between the recipient and the donor of a transplant), or by looking for the presence or absence of chromosome Y if the donor and the recipient of a transplant are of different sexes (which is done by cytogenetics or by FISH (fluorescence in situ hybridization)).

The HLA allele by which the population of human cells comprising antigen-specific T cells described herein is restricted (i.e., the HLA allele by which the antigen-specific T cells contained in the population of human cells comprising antigen-specific T cells are restricted) can be determined by any method known in the art, for example, as described in Trivedi et al., 2005, Blood 105:2793-2801; Barker et al., 2010, Blood 116:5045-5049; Hasan et al., 2009, J Immunol, 183:2837-2850; Doubrovina et al., 2012, Blood 120:1633-1646; International Patent Application Publication No. WO 2016/073550; International Patent Application Publication No. WO 2016/183153; International Patent Application Publication No. WO 2016/209816; or International Patent Application Publication No. WO 2017/044678. The determination can be performed using the population of human cells comprising antigen-specific T cells directly, an aliquot thereof, or a precursor cell population that indicates the HLA allele by which the population of human cells comprising antigen-specific T cells is restricted (i.e., the HLA allele by which the antigen-specific T cells contained in the population of human cells comprising antigen-specific T cells are restricted).

In some embodiments, the antigen-specific T cells contained in the population of human cells comprising antigen-specific T cells are restricted by an HLA allele shared with the tumor cells in the human patient to be treated. In a specific embodiment, this HLA allele restriction is ensured by ascertaining the HLA assignment of the tumor cells as described above, and selecting a population of human cells comprising antigen-specific T cells restricted by an HLA allele of such tumor cells. In another specific embodiment, when ascertaining the HLA assignment of the tumor cells is not possible and the human patient has not been the recipient of a transplant, this HLA allele restriction is ensured by ascertaining the HLA assignment of the human patient (e.g., by using non-tumor cells or tissue from the human patient), and selecting a population of human cells comprising antigen-specific T cells restricted by an HLA allele of the human patient. In another specific embodiment, when ascertaining the HLA assignment of the tumor cells is not possible and the human patient has been the recipient of a transplant, this HLA allele restriction is ensured by determining the origin of the tumor cells (whether transplant donor or recipient (i.e., the human patient)) as described above, ascertaining the HLA assignment of the origin of the tumor cells (transplant donor or the human patient, as the case may be), and selecting a population of human cells comprising antigen-specific T cells restricted by an HLA allele of the origin of the tumor cells. When determining the origin of the tumor cells is not possible in such embodiments, in a specific embodiment, this HLA allele restriction is ensured by ascertaining the HLA assignment of both the human patient and the transplant donor, and selecting a population of human cells comprising antigen-specific T cells restricted by an HLA allele shared by both the human patient and the transplant donor.

In other embodiments, the antigen-specific T cells contained in the population of human cells comprising antigen-specific T cells share at least 2 HLA alleles (for example, at least 2 out of 8 HLA alleles (such as two HLA-A alleles, two HLA-B alleles, two HLA-C alleles, and two HLA-DR alleles (e.g., two HLA-DRB1 alleles)), or preferably at least 2 out of 10 HLA alleles (such as two HLA-A alleles, two HLA-B alleles, two HLA-C alleles, two HLA-DR alleles (e.g., two HLA-DRB1 alleles), and two HLA-DQ alleles (e.g., two HLA-DQB1 alleles))) with the tumor cells in the human patient to be treated. In a specific embodiment, this sharing is ensured by ascertaining the HLA assignment of the tumor cells, and selecting a population of human cells comprising antigen-specific T cells that shares at least 2 HLA alleles (for example, at least 2 out of 8 HLA alleles (such as two HLA-A alleles, two HLA-B alleles, two HLA-C alleles, and two HLA-DR alleles (e.g., two HLA-DRB1 alleles)), or preferably at least 2 out of 10 HLA alleles (such as two HLA-A alleles, two HLA-B alleles, two HLA-C alleles, two HLA-DR alleles (e.g., two HLA-DRB1 alleles), and two HLA-DQ alleles (e.g., two HLA-DQB1 alleles))) with such tumor cells. In another specific embodiment, when ascertaining the HLA assignment of the tumor cells is not possible and the human patient has not been the recipient of a transplant, this sharing is ensured by ascertaining the HLA assignment of the human patient (e.g., by using non-tumor cells or tissue from the human patient), and selecting a population of human cells comprising antigen-specific T cells that shares at least 2 HLA alleles (for example, at least 2 out of 8 HLA alleles (such as two HLA-A alleles, two HLA-B alleles, two HLA-C alleles, and two HLA-DR alleles (e.g., two HLA-DRB1 alleles)), or preferably at least 2 out of 10 HLA alleles (such as two HLA-A alleles, two HLA-B alleles, two HLA-C alleles, two HLA-DR alleles (e.g., two HLA-DRB1 alleles), and two HLA-DQ alleles (e.g., two HLA-DQB1 alleles))) with the human patient. In another specific embodiment, when ascertaining the HLA assignment of the tumor cells is not possible and the human patient has been the recipient of a transplant, this sharing is ensured by determining the origin of the tumor cells (whether transplant donor or recipient (i.e., the human patient)) as described above, ascertaining the HLA assignment of the origin of the tumor cells (transplant donor or the human patient, as the case may be), and selecting a population of human cells comprising antigen-specific T cells that shares at least 2 HLA alleles (for example, at least 2 out of 8 HLA alleles (such as two HLA-A alleles, two HLA-B alleles, two HLA-C alleles, and two HLA-DR alleles (e.g., two HLA-DRB1 alleles)), or preferably at least 2 out of 10 HLA alleles (such as two HLA-A alleles, two HLA-B alleles, two HLA-C alleles, two HLA-DR alleles (e.g., two HLA-DRB1 alleles), and two HLA-DQ alleles (e.g., two HLA-DQB1 alleles))) with the origin of the tumor cells. When determining the origin of the tumor cells is not possible in such embodiments, in a specific embodiment, this sharing is ensured by ascertaining the HLA assignment of both the human patient and the transplant donor, and selecting a population of human cells comprising antigen-specific T cells that shares at least 2 HLA alleles (for example, at least 2 out of 8 HLA alleles (such as two HLA-A alleles, two HLA-B alleles, two HLA-C alleles, and two HLA-DR alleles (e.g., two HLA-DRB1 alleles)), or preferably at least 2 out of 10 HLA alleles (such as two HLA-A alleles, two HLA-B alleles, two HLA-C alleles, two HLA-DR alleles (e.g., two HLA-DRB1 alleles), and two HLA-DQ alleles (e.g., two HLA-DQB1 alleles))) with both the human patient and the transplant donor.

In other embodiments, the antigen-specific T cells contained in the population of human cells comprising antigen-specific T cells are restricted by an HLA allele shared with tumor cells in the human patient to be treated, and share at least 2 HLA alleles ((for example, at least 2 out of 8 HLA alleles (such as two HLA-A alleles, two HLA-B alleles, two HLA-C alleles, and two HLA-DR alleles (preferably two HLA-DRB1 alleles)), or preferably at least 2 out of 10 HLA alleles (such as two HLA-A alleles, two HLA-B alleles, two HLA-C alleles, two HLA-DR alleles (preferably two HLA-DRB1 alleles), and two HLA-DQ alleles (preferably two HLA-DQB1 alleles))) with the tumor cells in the human patient to be treated.

5.4. Composition and Kits

A population of human cells comprising antigen-specific T cells described herein can be stored in a pharmaceutical composition comprising a therapeutically effective amount of the population of human cells comprising antigen-specific T cells, and a pharmaceutically acceptable carrier.

The pharmaceutical acceptable carrier can be any physiologically-acceptable solution suitable for the storage and/or therapeutic administration of T cells, for example, a saline solution, a buffered saline solution, or a bio-compatible solution comprising one or more cryopreservatives (e.g., phosphate-buffered saline containing 7% DMSO, 5% dextrose and 1% dextran; hypothermosol containing 5% DMSO and 5% human serum albumin; normal saline containing 10% DMSO and 16% human serum albumin; or normal saline containing 10% DMSO and 15% human serum albumin).

The population of human cells comprising antigen-specific T cells can be stored in the pharmaceutical composition at any concentration desirable for its long-term storage and convenience of storage and handling. In a specific embodiment, the population of human cells comprising antigen-specific T cells is stored in the pharmaceutical composition at a concentration of about $5 \times 10^6$ cells/ml. In another specific embodiment, the population of human cells comprising antigen-specific T cells is stored in the pharmaceutical composition at a concentration of about $10 \times 10^6$ cells/ml. In another specific embodiment, the population of human cells comprising antigen-specific T cells is stored in the pharmaceutical composition at a concentration of about $20 \times 10^6$ cells/ml. In another specific embodiment, the population of human cells comprising antigen-specific T cells is stored in the pharmaceutical composition at a concentration of about $50 \times 10^6$ cells/ml. In another specific embodiment, the population of human cells comprising antigen-specific T cells is stored in the pharmaceutical composition at a concentration of about $100 \times 10^6$ cells/ml. In another specific embodiment, the population of human cells comprising antigen-specific T cells is stored in the pharmaceutical composition at a concentration of about $200 \times 10^6$ cells/ml. In another specific embodiment, the population of human cells comprising antigen-specific T cells is stored in the pharmaceutical composition at a concentration of about $500 \times 10^6$ cells/ml. In another specific embodiment, the population of human cells comprising antigen-specific T cells is stored in the pharmaceutical composition at a concentration of about 1 to $10 \times 10^6$ cells/ml. In another specific embodiment, the population of human cells comprising antigen-specific T cells is stored in the pharmaceutical composition at a concentration of about 10 to $100 \times 10^6$ cells/ml. In another specific embodiment, the population of human cells comprising antigen-specific T cells is stored in the pharmaceutical composition at a concentration of about 100 to $1000 \times 10^6$ cells/ml.

In a specific embodiment, the pharmaceutical composition is stored in a cryopreserved form before preparation for administration of the population of human cells to the human patient. For example, the pharmaceutical composition can be stored at a temperature of −150° C. or less, until just prior to preparation for administration. To prepare for intravenous administration, the cryopreserved pharmaceutical composition is thawed and optionally diluted in a sterile, nonpyrogenic isotonic solution (for example, Normosol® or PlasmaLyte®) to a final volume of up to 50 ml.

Also described herein are kits comprising in one or more containers the pharmaceutical composition described herein. In specific embodiments, the kits further comprise a second pharmaceutical composition comprising a second compound or biological product for treating the solid malignant tumor.

Optionally associated with such one or more containers can be a notice in the form prescribed by a governmental agency regulating the manufacture, use or sale of pharmaceuticals or biological products, which notice reflects approval by the agency of manufacture, use or sale for human administration. Also optionally associated with the one or more containers can be a notice about the potential risks for tumor flare.

The pharmaceutical compositions and kits described herein can be used in accordance with the methods of treating a solid malignant tumor and methods of improving safety in treatment of a solid malignant tumor as provided in this disclosure.

As stated above, the term "about" shall be construed so as to allow normal variation, such as, for example, a variation within 20%.

5.5. Solid Malignant Tumors, Antigen Specificity and Patients

In the adoptive immunotherapy methods described herein, a population of human cells comprising antigen-specific T cells that are specific for one or more antigens of a solid malignant tumor in the patient are administered. The antigen of a solid malignant tumor to which the T cells are specific can be a peptide or protein over-expressed in or on tumor cells of the solid malignant tumor relative to non-tumor cells (typically of the same tissue type as the tumor), or a peptide or protein that is uniquely expressed in or on tumor cells of the solid malignant tumor relative to non-tumor cells.

The solid malignant tumor can be, but is not limited to, a sarcoma, a carcinoma, a lymphoma, a germ cell tumor, or a blastoma.

In specific embodiments, the solid malignant tumor is a tumor of the breast, lung, ovary, stomach, pancreas, larynx, esophagus, testes, liver, parotid, biliary tract, colon, rectum, cervix, uterus, endometrium, kidney, bladder, prostate, thyroid, brain, or skin. In a specific embodiment, the solid malignant tumor is nasopharyngeal carcinoma, gastric cancer, or leiomyosarcoma.

In specific embodiments, the solid malignant tumor is a lymphoproliferative disorder (LPD). In a specific embodiment, the LPD is a lymphoma, such as, for example, a B-cell lymphoma, a T-cell lymphoma, an NK/T lymphoma, a Burkitt lymphoma, a Hodgkin lymphoma or a Non-Hodgkin lymphoma. In a specific embodiment, the lymphoma is diffuse large B-cell lymphoma (DLBCL) (for example, a non-germinal center B cell-like DLBCL). In another specific embodiment, the lymphoma is plasmablastic lymphoma (PBL).

In some embodiments, the anatomic site of the solid malignant tumor is inside the lymph nodes. In other embodiments, the anatomic site of the solid malignant tumor is outside the lymph nodes. In a particular embodiment, the solid malignant tumor is an HIV-associated Non-Hodgkin lymphoma with involvement in an organ such as liver, gastrointestinal track, or subcutaneous soft tissue, or is a leptomeningeal disease, and the anatomic site of the solid malignant tumor is outside the lymph nodes.

In a specific embodiment, the anatomic site of the solid malignant tumor is within the head and neck region. In a further specific embodiment, the anatomic site of the solid malignant tumor is within the neck.

In a specific embodiment, the anatomic site of the solid malignant tumor is inside the neck lymph nodes. In a further specific embodiment, the anatomic site of the solid malignant tumor is inside the left neck lymph nodes. In a particular embodiment, the anatomic site of the solid malignant tumor is inside the left neck lymph nodes at levels 2, 3 and 5.

In various embodiments, the human patient has been immunocompromised.

In specific embodiments, the human patient is a recipient of a transplant. In some embodiments, the human patient is a recipient of a solid organ transplant. The solid organ transplant can be, but is not limited to, a kidney transplant, a liver transplant, a heart transplant, an intestinal transplant, a pancreas transplant, a lung transplant, a small bowel transplant, or a combination thereof. In other embodiments, the human patient is a recipient of a hematopoietic stem cell transplant (HSCT), for example, a T-cell depleted HSCT. The HSCT can be a bone marrow transplant, a peripheral blood stem cell transplant, or a cord blood transplant.

In specific embodiments, the human patient is a HIV-infected. In a specific embodiment, the human patient has acquired immunodeficiency syndrome (AIDS).

In specific embodiments, the human patient has received immunosuppressant therapy (for example, after solid organ transplant).

In specific embodiments, the human patient has a primary immunodeficiency (for example, a genetic disorder that has caused immunodeficiency).

In some embodiments, the solid malignant tumor is positive for Epstein-Barr virus (EBV) and the one or more antigens are one or more antigens of EBV, such as, for example, EBNA1, EBNA2, EBNA3A, EBNA3B, EBNA3C, LMP1, and/or LMP2. In a specific embodiment, the solid malignant tumor is an EBV-positive LPD such as an EBV-positive lymphoma and the one or more antigens are one or more antigens of EBV, such as, for example, EBNA1, EBNA2, EBNA3A, EBNA3B, EBNA3C, LMP1, and/or LMP2. In a particular aspect of the specific embodiment, the solid malignant tumor is an HIV-associated EBV-positive LPD such as an HIV-associated EBV-positive lymphoma and the one or more antigens are one or more antigens of EBV, such as, for example, EBNA1, EBNA2, EBNA3A, EBNA3B, EBNA3C, LMP1, and/or LMP2. In a further particular aspect of the specific embodiment, the solid malignant tumor is an HIV-associated EBV-positive LPD such as an HIV-associated EBV-positive lymphoma that is within the neck (for example, inside the neck lymph nodes), and the one or more antigens are one or more antigens of EBV, such as, for example, EBNA1, EBNA2, EBNA3A, EBNA3B, EBNA3C, LMP1, and/or LMP2. In another specific embodiment, the solid malignant tumor is an EBV-positive nasopharyngeal carcinoma and the one or more antigens are one or more antigens of EBV, such as, for example, EBNA1, EBNA2, EBNA3A, EBNA3B, EBNA3C, LMP1, and/or LMP2. In another specific embodiment, the solid malignant tumor is an EBV-positive gastric cancer and the one or more antigens are one or more antigens of EBV, such as, for example, EBNA1, EBNA2, EBNA3A, EBNA3B, EBNA3C, LMP1, and/or LMP2. In another specific embodiment, the solid malignant tumor is an EBV-positive leiomyosarcoma and the one or more antigens are one or more antigens of EBV, such as, for example, EBNA1, EBNA2, EBNA3A, EBNA3B, EBNA3C, LMP1, and/or LMP2.

In other embodiments, the solid malignant tumor is positive for cytomegalovirus (CMV) and the one or more antigens are one or more antigens of CMV, such as CMV pp65 and/or CMV IE1. In a specific embodiment, the solid malignant tumor is CMV-positive glioblastoma multiforme and the one or more antigens are one or more antigens of CMV, such as CMV pp65 and/or CMV IE1.

In other embodiments, the solid malignant tumor is positive for Wilms tumor 1 (WT1) and the one or more antigens is WT1.

In a specific embodiment, the human patient is an adult (at least age 16). In another specific embodiment, the human patient is an adolescent (age 12-15). In another specific embodiment, the patient is a child (under age 12).

6. EXAMPLES

Certain embodiments provided herein are illustrated by the following non-limiting examples. Example 1 describes tumor flare observed in a patient whose HIV-associated EBV-positive lymphoma was treated with EBV-specific T cells. Example 2 provides non-limiting exemplary instructions to physicians for use of antigen-specific T cells in treatment of a solid malignant tumor in a Package Leaflet.

6.1. Example 1

A 34 year-old Caucasian male was enrolled in an expanded access study using allogeneic Epstein-Barr Virus-specific cytotoxic T lymphocytes (EBV-CTLs), generated by ex vivo sensitization, for treating patients with EBV-associated viremia or malignancies.

The patient's medical and surgical history included HIV infection diagnosed 242 days prior to the start of EBV-CTLs, and HIV-associated EBV$^+$ diffuse large B cell lymphoma (DLBCL), non-germinal center B cell-like (non-GCB), diagnosed about 7 months prior to the start of EBV-CTLs, with Epstein-Barr virus-encoded small RNAs (EBER) positivity confirmed by biopsies. Imaging studies for lymphoma staging showed the presence of disease in the left anterior cervical area and nasopharynx. Laboratory test results near the time of lymphoma diagnosis included a CD4 count of 118 cells/mm$^3$ (measured 219 days prior to the start of EBV-CTLs). A follow-up CD4 count measured 10 days prior to the start of EBV-CTLs remained unchanged at 118 cells/mm$^3$. EBV DNA by polymerase chain reaction (PCR) was 20,044 copies/mL on the starting day of EBV-CTLs.

Concomitant medications taken at the time of the event included acyclovir, allopurinol, azithromycin, ciprofloxacin, citalopram, docusate, dolutegravir, emtricitabine-tenofovir, gabapentin, itraconazole, lidocaine-prilocaine cream, loratadine, melatonin, ENSURE PLUS® (nutritional supplements), ondansetron, oxycodone, polyethylene glycol pack, prochlorperazine, promethazine HCL, senna, and sulfamethoxazole-trimethoprim. The patient has drug allergies to lamotrigine (rash) and ibuprofen (rash).

The patient's previous chemotherapies included 6 cycles of dose-adjusted rituximab/etoposide/prednisolone/Oncovin (vincristine)/cyclophosphamide/hydroxydaunorubicin (DA-REPOCH); 1 cycle of rituximab/ifosphamide/etoposide/cytarabine (RIVAC). The LDH at the time of disease progression following RIVAC was 800 IU/ml. The patient also received 2 cycles of rituximab/gemcitabine/dexamethasone/Platinol® (cisplatin) (RGDP) as salvage chemotherapy. Lymphoma disease progression was confirmed via PET scan 17 days prior to the start of EBV-CTLs with disease present in the right nasopharynx and the left posterior triangle with invasion into the sternocleidomastoid muscle.

The patient received his initial intravenous (IV) infusion of a human cell product enriched for EBV-specific CTLs at a dose of 2×10$^6$ cells/kg. Dose 2 was administered 7 days after the first dose; dose 3 was administered 7 days after the second dose.

Administration of the first dose of EBV-specific CTLs was notable for increased size of neck lymph nodes known to be involved with lymphoma within a day of the infusion of the cells. No adverse events were reported for this dose.

After the second dose of EBV-specific CTLs was administered, on that day, the patient was found to have increased swelling in the neck coincident with areas of disease involvement approximately 1 hour post-infusion, and was admitted for observation the same day. There was concern for airway compromise if the swelling persisted. He was diagnosed with grade 3 tumor flare. There was no stridor, nor tumor lysis syndrome. There was no evidence for cytokine release syndrome with no changes in temperature nor other vital signs. No scans, biopsies, or other tests were performed on the tumor flare. EBV DNA rose to and peaked at 244,132 copies/mL. Laboratory results on the day of admission showed blood lactate dehydrogenase (LDH) of 403 U/L (reference values 100-190 U/L), and hemoglobin (HGB) of 10.8 g/dL (reference values 13.2-17.3 g/dL). Treatment for the tumor flare was limited to pain medication (Dilaudid® (hydromorphone)) and dressing changes for an open necrotic wound on the neck as needed for comfort. No action was taken with study drug in response to the event.

Computerized tomography (CT) scan one day after administration of the second dose of EBV-specific CTLs showed increased size of a conglomerate lymph node mass measuring 8.6 cm×4.7 cm, previously measuring 6.6 cm×3.4 cm at baseline, accompanied by increased intratumoral necrosis.

Two days after administration of the second dose of EBV-specific CTLs, repeat laboratory tests revealed LDH of 377 U/L, HGB of 9.9 g/dL and platelet count of 149 K/uL (reference values 150-400 K/uL). On that same day, the outcome of the tumor flare was reported as resolving, and the patient was discharged from the hospital.

After the third dose of EBV-specific CTLs, tumor enlargement was noted once again transiently but was less pronounced than after dose 2. EBV DNA declined to 91,046 copies/mL 10 days after administration of the third dose of EBV-specific CTLs.

Images of the patient's lymphoma and tumor flare are shown in FIG. 1. Imaging on the day after the second dose of EBV-specific CTLs were administered showed necrosis within the cervical lymph nodes involved with disease.

This case demonstrates a vigorous and rapid response by EBV-specific CTLs to HIV-associated EBV$^+$ DLBCL in a patient with chemotherapy refractory disease. The exuberant response was not associated with cytokine release syndrome, infusion reaction, or tumor lysis syndrome.

6.2. Example 2: Instructing the Physician—Package Leaflet

By way of example, but not limitation, instructions to physicians for use of antigen-specific T cells in treatment of a solid malignant tumor in a Package Leaflet can be as follows:

Warnings and Precautions

The product's effects may include rapid tumor response leading to anatomic swelling of the tumor (i.e., tumor flare). Physicians should inform patients about the potential risks and benefits of the product, including the potential risks for tumor flare depending on the anatomic site of their tumor. Tell your patients to contact you if tumor swelling occurs. Counsel patients with Waldeyer's ring lymphadenopathy to contact you if shortness of breath or stridor occurs.

Grade and manage tumor flare according to the following Table:

| Tumor Flare Severity | Evaluation | Intervention |
| --- | --- | --- |
| Grade 1 | Asymptomatic, clinical or diagnostic observations only | No intervention |
| Grade 2 | Symptomatic; medical intervention indicated | Medical treatment (e.g., pain medication; antibiotics for necrotic tumor) |

-continued

| Tumor Flare Severity | Evaluation | Intervention |
| --- | --- | --- |
| Grade 3 | Stridor, respiratory distress; hospitalization indicated | Hospitalization with monitoring as appropriate for the anatomic tumor site |
| Grade 4 | Life-threatening airway compromise; urgent intervention indicated | Intubation to protect the airway if appropriate; other intervention according to the anatomic tumor site |
| Grade 5 | Death | — |

7. INCORPORATION BY REFERENCE

All references cited herein are incorporated herein by reference in their entirety and for all purposes to the same extent as if each individual publication or patent or patent application was specifically and individually indicated to be incorporated by reference in its entirety for all purposes.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. A method of treating a solid malignant tumor in a human patient comprising the following steps in the order stated: (a) administering to the human patient a population of human cells comprising antigen-specific T cells that are specific for one or more antigens of the solid malignant tumor, said antigen-specific T cells having been generated by ex vivo sensitizing human T cells to the one or more antigens, wherein the antigen-specific T cells are not genetically engineered to be specific for the one or more antigens, wherein the population of human cells contains at least 70% T cells, and wherein the solid malignant tumor is a lymphoma; (b) grading tumor flare in the human patient as Grade 2, 3, or 4 according to the Evaluation column in the following Table, wherein the tumor flare is a clinical reaction to the administration of the population of human cells that is manifested as swelling of the tumor; and (c) managing tumor flare in the human patient according to the Intervention column in the following Table:

| Tumor Flare Severity | Evaluation | Intervention |
| --- | --- | --- |
| Grade 2 | Symptomatic; medical intervention indicated | Medical treatment |
| Grade 3 | Stridor, respiratory distress; hospitalization indicated | Hospitalization with monitoring as appropriate for the anatomic tumor site |
| Grade 4 | Life-threatening airway compromise; urgent intervention indicated | Intubation to protect the airway if appropriate; other intervention according to the anatomic tumor site. |

2. The method of claim 1, wherein after said administering the human patient develops tumor flare that is Grade 2 tumor flare; and the method comprises treating the tumor flare medically.

3. The method of claim 2, wherein the step of treating the tumor flare medically comprises providing one or more pain medications to the human patient.

4. The method of claim 3, wherein the one or more pain medications comprise a nonsteroidal anti-inflammatory drug (NSAID).

5. The method of claim 1, wherein after said administering the human patient develops tumor flare that is Grade 3 tumor flare; and the method comprises hospitalizing the human patient and monitoring the human patient as appropriate for the anatomic tumor site.

6. The method of claim 1, wherein after said administering the human patient develops tumor flare that is Grade 4 tumor flare; and the method comprises intubating the human patient to protect the airway or performing another intervention according to the anatomic tumor site.

7. In a method of treating a solid malignant tumor in a human patient that comprises administering to the human patient a population of human cells comprising antigen-specific T cells that are specific for one or more antigens of the solid malignant tumor, said antigen-specific T cells having been generated by ex vivo sensitizing human T cells to the one or more antigens, wherein the antigen-specific T cells are not genetically engineered to be specific for the one or more antigens, wherein the population of human cells contains at least 70% T cells, and wherein the solid malignant tumor is a lymphoma, wherein the improvement comprises: (a) grading tumor flare in the human patient as Grade 2, 3, or 4 according to the Evaluation column in the following Table, wherein the tumor flare is a clinical reaction to the administration of the population of human cells that is manifested as swelling of the tumor; and (b) managing tumor flare in the human patient according to the Intervention column in the following Table:

| Tumor Flare Severity | Evaluation | Intervention |
| --- | --- | --- |
| Grade 2 | Symptomatic; medical intervention indicated | Medical treatment |
| Grade 3 | Stridor, respiratory distress; hospitalization indicated | Hospitalization with monitoring as appropriate for the anatomic tumor site |
| Grade 4 | Life-threatening airway compromise; urgent intervention indicated | Intubation to protect the airway if appropriate; other intervention according to the anatomic tumor site. |

8. A method of treating a solid malignant tumor in a human patient comprising: (a) administering to the human patient a population of human cells comprising antigen-specific T cells that are specific for one or more antigens of the solid malignant tumor, said antigen-specific T cells having been generated by ex vivo sensitizing human T cells to the one or more antigens, wherein the antigen-specific T cells are not genetically engineered to be specific for the one or more antigens, wherein the population of human cells contains at least 70% T cells, and wherein the solid malignant tumor is a lymphoma; (b) monitoring the human patient for an indication of tumor flare, wherein the tumor flare is a clinical reaction to the administration of the population of human cells that is manifested as swelling of the tumor; (c) grading tumor flare in the human patient as Grade 2, 3, or 4 according to the Evaluation column in the following Table; and (d) managing tumor flare in the human patient according to the Intervention column in the following Table:

| Tumor Flare Severity | Evaluation | Intervention |
| --- | --- | --- |
| Grade 2 | Symptomatic; medical intervention indicated | Medical treatment |
| Grade 3 | Stridor, respiratory distress; hospitalization indicated | Hospitalization with monitoring as appropriate for the anatomic tumor site |
| Grade 4 | Life-threatening airway compromise; urgent intervention indicated | Intubation to protect the airway if appropriate; other intervention according to the anatomic tumor site. |

9. The method of claim 8, wherein the administering step is by bolus intravenous infusion.

10. The method of claim 8, which further comprises stopping treatment of the human patient with the population of human cells because the human patient has developed tumor flare that is life-threatening or deemed an excessive risk by the treating physician.

11. The method of claim 8, wherein the lymphoma is diffuse large B-cell lymphoma (DLBCL).

12. The method of claim 8, wherein the lymphoma is plasmablastic lymphoma (PBL).

13. The method of claim 8, wherein the solid malignant tumor is positive for Epstein-Barr virus (EBV) and the one or more antigens are one or more antigens of EBV.

14. The method of claim 8, wherein the anatomic site of the solid malignant tumor is inside the lymph nodes.

15. The method of claim 14, wherein the anatomic site of the solid malignant tumor is inside the neck lymph nodes.

16. The method of claim 8, wherein the anatomic site of the solid malignant tumor is within the head and neck region.

17. The method of claim 16, wherein the anatomic site of the solid malignant tumor is within the neck.

18. The method of claim 8, wherein the population of human cells comprising antigen-specific T cells is derived from a human donor that is allogeneic to the human patient.

19. The method of claim 8, wherein after said administering the human patient develops tumor flare that is Grade 2 tumor flare, wherein the method comprises treating the tumor flare medically, wherein the step of treating the tumor flare medically comprises providing one or more pain medications to the human patient, and wherein the one or more pain medications comprise an NSAID.

20. In a method of treating a solid malignant tumor in a human patient that comprises administering to the human patient a population of human cells comprising antigen-specific T cells that are specific for one or more antigens of the solid malignant tumor, said antigen-specific T cells having been generated by ex vivo sensitizing human T cells to the one or more antigens, wherein the antigen-specific T cells are not genetically engineered to be specific for the one or more antigens, wherein the population of human cells contains at least 70% T cells, and wherein the solid malignant tumor is a lymphoma, wherein the improvement comprises: (a) monitoring the human patient for an indication of tumor flare, wherein the tumor flare is a clinical reaction to the administration of the population of human cells that is manifested as swelling of the tumor; (b) grading tumor flare in the human patient as Grade 2, 3, or 4 according to the Evaluation column in the following Table; and (c) managing tumor flare in the human patient according to the Intervention column in the following Table:

| Tumor Flare Severity | Evaluation | Intervention |
| --- | --- | --- |
| Grade 2 | Symptomatic; medical intervention indicated | Medical treatment |
| Grade 3 | Stridor, respiratory distress; hospitalization indicated | Hospitalization with monitoring as appropriate for the anatomic tumor site |
| Grade 4 | Life-threatening airway compromise; urgent intervention indicated | Intubation to protect the airway if appropriate; other intervention according to the anatomic tumor site. |

21. A method of treating a solid malignant tumor in a human patient comprising: (a) administering to the human patient a population of human cells comprising antigen-specific T cells that are specific for one or more antigens of the solid malignant tumor, said antigen-specific T cells having been generated by ex vivo sensitizing human T cells to the one or more antigens, wherein the antigen-specific T cells are not genetically engineered to be specific for the one or more antigens, wherein the population of human cells contains at least 70% T cells, and wherein the solid malignant tumor is a lymphoma; (b) monitoring the human patient for an indication of tumor flare, wherein the tumor flare is a clinical reaction to the administration of the population of human cells that is manifested as swelling of the tumor; (c) stopping treatment of the human patient with the population of human cells because the human patient has developed tumor flare that is life-threatening or deemed an excessive risk by the treating physician; and (d) re-initiating treatment of the human patient with the population of human cells when the tumor flare subsides or decreases after stopping treatment.

22. The method of claim 21, wherein the solid malignant tumor is positive for EBV and the one or more antigens are one or more antigens of EBV.

23. The method of claim 21, wherein the lymphoma is DLBCL.

24. The method of claim 21, wherein the lymphoma is PBL.

25. In a method of treating a solid malignant tumor in a human patient that comprises administering to the human patient a population of human cells comprising antigen-specific T cells that are specific for one or more antigens of the solid malignant tumor, said antigen-specific T cells having been generated by ex vivo sensitizing human T cells to the one or more antigens, wherein the antigen-specific T cells are not genetically engineered to be specific for the one or more antigens, wherein the population of human cells contains at least 70% T cells, and wherein the solid malignant tumor is a lymphoma, wherein the improvement comprises: (a) monitoring the human patient for an indication of tumor flare, wherein the tumor flare is a clinical reaction to the administration of the population of human cells that is manifested as swelling of the tumor; (b) stopping treatment of the human patient with the population of human cells because the human patient has developed tumor flare that is life-threatening or deemed an excessive risk by the treating physician; and (c) re-initiating treatment of the human patient with the population of human cells when the tumor flare subsides or decreases after stopping treatment.

\* \* \* \* \*